US011980625B2

(12) United States Patent
Aimetti et al.

(10) Patent No.: US 11,980,625 B2
(45) Date of Patent: *May 14, 2024

(54) GANAXOLONE FOR USE IN TREATING TUBEROUS SCLEROSIS COMPLEX

(71) Applicant: Marinus Pharmaceuticals, Inc., Radnor, PA (US)

(72) Inventors: Alex Aimetti, Radnor, PA (US); Joseph Hulihan, Radnor, PA (US); Scott Braunstein, Radnor, PA (US)

(73) Assignee: Marinus Pharmaceuticals, Inc., Radnor, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,048

(22) Filed: Apr. 26, 2023

(65) Prior Publication Data

US 2024/0100067 A1    Mar. 28, 2024

Related U.S. Application Data

(63) Continuation of application No. 17/683,624, filed on Mar. 1, 2022, now Pat. No. 11,701,367, which is a continuation of application No. PCT/US2020/063648, filed on Dec. 7, 2020.

(60) Provisional application No. 62/944,549, filed on Dec. 6, 2019.

(51) Int. Cl.
*A61K 31/57* (2006.01)
*A61P 25/08* (2006.01)

(52) U.S. Cl.
CPC .............. *A61K 31/57* (2013.01); *A61P 25/08* (2018.01)

(58) Field of Classification Search
CPC .................................. A61K 31/57; A61P 25/08
See application file for complete search history.

(56) References Cited

U.S. PATENT DOCUMENTS

| | | |
|---|---|---|
| 2,671,750 A | 3/1954 | Macek |
| 4,540,602 A | 9/1985 | Motoyama et al. |
| 4,783,484 A | 11/1988 | Violanto et al. |
| 4,826,689 A | 5/1989 | Violanto et al. |
| 4,997,454 A | 3/1991 | Violante et al. |
| 5,134,127 A | 7/1992 | Stella et al. |

(Continued)

FOREIGN PATENT DOCUMENTS

| | | |
|---|---|---|
| EP | 169618 A2 | 1/1986 |
| EP | 498824 A1 | 8/1992 |

(Continued)

OTHER PUBLICATIONS

Fabian, "Azabenzenes (azines)—The nitrogen derivatives of benzene with one to six N atoms: Stability. homodesmotic stabilization energy, electron distribution, and magnetic ring current; a computational study" Canadian J. Chem, 2004, 82, 50-69.

(Continued)

*Primary Examiner* — San Ming R Hui
(74) *Attorney, Agent, or Firm* — Hogan Lovells US LLP

(57) ABSTRACT

The disclosure to methods for treating tuberous sclerosis complex or tuberous sclerosis complex-related epilepsy, comprising administering to a subject in need thereof a therapeutically effective amount of a pharmaceutically acceptable pregnenolone neurosteroid, such as ganaxolone, to reduce one or more symptoms of tuberous sclerosis complex or tuberous sclerosis complex-related epilepsy.

25 Claims, 2 Drawing Sheets

(56) References Cited

U.S. PATENT DOCUMENTS

| | | |
|---|---|---|
| 5,145,684 A | 9/1992 | Liversidge et al. |
| 5,209,746 A | 5/1993 | Balahan et al. |
| 5,213,808 A | 5/1993 | Bar-Shalom et al. |
| 5,221,278 A | 6/1993 | Linkwitz et al. |
| 5,260,068 A | 11/1993 | Chen |
| 5,260,069 A | 11/1993 | Chen |
| 5,298,262 A | 3/1994 | Na et al. |
| 5,299,131 A | 3/1994 | Haas et al. |
| 5,308,348 A | 5/1994 | Balaban et al. |
| 5,312,390 A | 5/1994 | Wong |
| 5,318,588 A | 6/1994 | Horzewski et al. |
| 5,340,590 A | 8/1994 | Wong et al. |
| 5,346,702 A | 9/1994 | Na et al. |
| 5,352,459 A | 10/1994 | Hollister et al. |
| 5,356,476 A | 10/1994 | Oshlack et al. |
| 5,376,645 A | 12/1994 | Stella et al. |
| 5,391,381 A | 2/1995 | Wong et al. |
| 5,399,363 A | 3/1995 | Liversidge et al. |
| 5,429,824 A | 7/1995 | June |
| 5,445,829 A | 8/1995 | Paradissis et al. |
| 5,456,679 A | 10/1995 | Balaban et al. |
| 5,470,583 A | 11/1995 | Na et al. |
| 5,472,708 A | 12/1995 | Chen |
| 5,494,683 A | 2/1996 | Liversidge et al. |
| 5,508,040 A | 4/1996 | Chen |
| 5,510,118 A | 4/1996 | Bosch et al. |
| 5,518,187 A | 5/1996 | Bruno et al. |
| 5,534,270 A | 7/1996 | De Castro |
| 5,543,133 A | 8/1996 | Swanson |
| 5,556,847 A | 9/1996 | Johnson et al. |
| 5,560,932 A | 10/1996 | Bagchi et al. |
| 5,573,783 A | 11/1996 | Desieno et al. |
| 5,629,277 A | 5/1997 | Plishka |
| 5,662,883 A | 9/1997 | Bagchi et al. |
| 5,665,331 A | 9/1997 | Bagchi et al. |
| 5,718,388 A | 2/1998 | Czekai et al. |
| 5,741,522 A | 4/1998 | Violante et al. |
| 5,776,496 A | 7/1998 | Violante et al. |
| 5,840,329 A | 11/1998 | Bai |
| 5,888,996 A | 3/1999 | Farb |
| 5,862,999 A | 11/1999 | Czekai et al. |
| 5,980,508 A | 11/1999 | Cardanibe et al. |
| 6,039,979 A | 3/2000 | Gendrot et al. |
| 6,161,536 A | 12/2000 | Redmon et al. |
| 6,214,379 B1 | 4/2001 | Hermelin |
| 6,228,398 B1 | 5/2001 | Devane et al. |
| 6,248,363 B1 | 6/2001 | Patel et al. |
| 6,264,922 B1 | 7/2001 | Wood |
| 6,267,989 B1 | 7/2001 | Liversidge et al. |
| 6,316,029 B1 | 11/2001 | Jain et al. |
| 6,375,986 B1 | 4/2002 | Ryde et al. |
| 6,423,746 B1 | 7/2002 | Yarbrough et al. |
| 6,428,814 B1 | 8/2002 | Bosch |
| 6,432,381 B2 | 8/2002 | Liversidge et al. |
| 6,514,518 B2 | 2/2003 | Monkhouse et al. |
| 6,569,463 B2 | 5/2003 | Patel et al. |
| 6,592,903 B2 | 7/2003 | Ryde et al. |
| 6,607,751 B1 | 8/2003 | Odidi et al. |
| 6,627,223 B2 | 9/2003 | Percel et al. |
| 6,682,759 B2 | 1/2004 | Lim et al. |
| 6,689,378 B1 | 2/2004 | Sun et al. |
| 6,730,325 B2 | 5/2004 | Devane et al. |
| 6,793,936 B2 | 9/2004 | Devane et al. |
| 6,902,742 B2 | 6/2005 | Devane et al. |
| 6,908,626 B2 | 6/2005 | Cooper et al. |
| 6,923,988 B2 | 8/2005 | Patel et al. |
| 6,969,529 B2 | 11/2005 | Bosch |
| 6,976,647 B2 | 12/2005 | Reed et al. |
| 7,078,057 B2 | 7/2006 | Kerkhof |
| 7,198,795 B2 | 4/2007 | Cooper et al. |
| 7,550,445 B2 | 6/2009 | Nerurkar et al. |
| 7,858,609 B2 | 12/2010 | Shaw et al. |
| 8,022,054 B2 | 9/2011 | Shaw et al. |
| 8,318,714 B2 | 11/2012 | Shaw et al. |
| 8,362,286 B2 | 1/2013 | Shaw et al. |
| 8,367,651 B2 | 2/2013 | Shaw et al. |
| 8,604,011 B2 | 12/2013 | Mellon |
| 8,618,087 B2 | 12/2013 | Shaw et al. |
| 8,658,692 B2 | 2/2014 | Kim et al. |
| 9,029,355 B2 | 5/2015 | Shaw et al. |
| 9,056,116 B2 | 6/2015 | Shaw et al. |
| 9,629,853 B2 | 4/2017 | Jones et al. |
| 10,391,105 B2 | 8/2019 | Cashman et al. |
| 10,603,308 B2 | 3/2020 | During |
| 2002/0012675 A1 | 1/2002 | Jain et al. |
| 2002/0150616 A1 | 10/2002 | Vandercruys |
| 2003/0054042 A1 | 3/2003 | Liversidge et al. |
| 2003/0129242 A1 | 7/2003 | Bosch et al. |
| 2003/0215502 A1 | 11/2003 | Pruss et al. |
| 2004/0067251 A1 | 4/2004 | Johnston et al. |
| 2004/0105889 A1 | 6/2004 | Ryde et al. |
| 2004/0214746 A1 | 10/2004 | Bosch et al. |
| 2004/0224020 A1 | 11/2004 | Schoenhard |
| 2004/0258757 A1 | 12/2004 | Bosch et al. |
| 2005/0031691 A1 | 2/2005 | McGuirk et al. |
| 2005/0118268 A1 | 6/2005 | Percel et al. |
| 2005/0181050 A1 | 8/2005 | Hirsch et al. |
| 2005/0226927 A1 | 10/2005 | Han et al. |
| 2005/0232890 A1 | 10/2005 | Hoath et al. |
| 2006/0003005 A1 | 1/2006 | Cao et al. |
| 2006/0216353 A1 | 9/2006 | Liversidge et al. |
| 2007/0141161 A1 | 6/2007 | Shaw et al. |
| 2007/0148252 A1 | 6/2007 | Shaw et al. |
| 2009/0004262 A1 | 1/2009 | Shaw et al. |
| 2011/0236487 A1 | 9/2011 | Shaw et al. |
| 2012/0052098 A1 | 3/2012 | Shaw et al. |
| 2012/0316146 A1 | 12/2012 | Goodchild et al. |
| 2014/0057885 A1 | 2/2014 | Reddy et al. |
| 2014/0235600 A1 | 8/2014 | Covey et al. |
| 2014/0249120 A1 | 9/2014 | Covey et al. |
| 2015/0018327 A1 | 1/2015 | Reddy et al. |
| 2015/0158903 A1 | 6/2015 | Upasani et al. |
| 2015/0175651 A1 | 6/2015 | Salituro et al. |
| 2015/0291654 A1 | 10/2015 | Upasani et al. |
| 2015/0313915 A1 | 11/2015 | Rogawski et al. |
| 2015/0315230 A1 | 11/2015 | Covey et al. |
| 2016/0228454 A1 | 8/2016 | Zhang et al. |
| 2017/0285512 A1 | 9/2017 | Zhang et al. |
| 2017/0348327 A1 | 12/2017 | Kanes et al. |
| 2018/0071315 A1 | 3/2018 | Cashman et al. |
| 2019/0160078 A1 | 5/2019 | Masuoka et al. |

FOREIGN PATENT DOCUMENTS

| | | |
|---|---|---|
| EP | 499299 A2 | 8/1992 |
| EP | 580690 A1 | 2/1994 |
| WO | 9526715 A2 | 10/1995 |
| WO | 9857648 A1 | 12/1998 |
| WO | 145677 A1 | 6/2001 |
| WO | 2007062266 A1 | 5/2007 |
| WO | 2011088503 A1 | 7/2011 |
| WO | 2014085668 A1 | 6/2014 |
| WO | 2014127201 A1 | 6/2014 |
| WO | 2014160441 A1 | 10/2014 |
| WO | 2014160480 A1 | 10/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A1 | 1/2015 |
| WO | 2015081170 | 6/2015 |
| WO | 2015187988 A1 | 10/2015 |
| WO | 2015180679 A1 | 12/2015 |
| WO | 2015187988 | 12/2015 |
| WO | 2016040322 A1 | 3/2016 |
| WO | 2016127170 A1 | 8/2016 |
| WO | 2017066626 A1 | 4/2017 |
| WO | 2017156103 | 9/2017 |
| WO | 2017156103 A1 | 9/2017 |

(56) References Cited

FOREIGN PATENT DOCUMENTS

| WO | 2018195186 A1 | 10/2018 |
|---|---|---|
| WO | 2020118142 A1 | 6/2020 |

OTHER PUBLICATIONS

Bialer et al., (2010), "Progress report on new antiepileptic drugs: A summary of the Tenth Eilat Conference (EILAT X)," Epilepsy Research, 92, pp. 89-124.
Cope, et al., (2009), "Enhanced tonic GABAA inhibition in typical absence epilepsy," Nat. Med., 15(12): 1392-1398.
"Marinus Epilepsy Candidate Ganaxolone Fails Phase III Trial," https://www.genengnews.com/news/marinus-epilepsy-candidate-ganaxolone-fails-phase-iii-trial/, Genetic Engineering & Biotechnology News, Jun. 13, 2016.
Reddy et al. "Neurosteroids—Endogenous Regulators of Seizure Susceptibility and Role in the Treatment of Epilepsy", Jasper's Basic Mechanisms of the Epilepsies, 2012.
Tan et al., "Mutations of protocadherin 19 in female epilepsy (PCDH19-FE) lead to allopregnanolone deficiency." Human Molecular Genetics, 2015; vol. 24(18); pp. 5250-5259.
Fabian, "Azabenzenes (azines)—The nitrogen derivatives of benzene with one to six N atoms: Stabiiity. homodesmotic stabilization energy, electron distribution, and magnetic ring current; a computational study" Canadian J. Chem, 2004, 82, 50-69.
Pieribone, et al., "Clinical Evaluation of Ganaxolone in Pediatric and Adolescent Patients with Refractory Epilepsy" Epilepsia, vol. 48(10), 5 pages (2007).
Marinus Pharmaceuticals, "Marinus Pharmaceuticals, Inc. enters into use agreement with CyDex Pharmaceuticals, Inc. for use of Captisol® for Ganaxolone IV," Aug. 12, 2014, Retrieved from the Internet: URL: http://ir.marinuspharma.com/releasedetail.cfm?release id_065715.
Monaghan et al., "Initial Human Experience with Ganaxolone, a Neuroactive Steroid with Antiepileptic Activity" Epilepsia, vol. 38(9), pp. 1026-1031 (1997).
Mula, "Emerging drugs for focal epilepsy." Expert Opinion on Emerging Drugs, 18(1):87-95, (2013).
Sham et al., "Formulation and characterization of spray-dried powders containing nanoparticles for aerosol delivery to the lung", International Journal of Pharmaceuticals, vol. 269, pp. 45 (2004).
Valotis et al., "Human Receptor Kinetics, Tissue Binding Affinity, and Stability of Mometasone Furoate" Journal of Pharmaceutical Sciences, vol. 93(5). 14 Pages.
Loftsson et al. "Cyclodextrins in drug review," Expert Opinion, (Mar. 2005).
Hogenkamp et al., "Synthesis and in Vitro Activity of 3Beta-Substituted-3Alpha-hydroxypregnan-20-ones:Allocteric Modulations of the GABA(A) Receptor"; J. Med. Chem., 40; pp. 61-72 (1997).
Nohria et al., "Ganaxolone"; The Journal of the American Society for Experimental NeuroTherapeutics; vol. 4; pp. 102-105 (2004).
Pramanick et al., "Excipient Selection In Parenteral Formulation Development"; Pharma Times, vol. 45(3); pp. 65-77 (2013).
Rogawski et al., "Neuroactive Steroids for the Treatment of Status Epilepticus"; Epilepspia, vol. 54(6); pp. 93-98 (2013).
Rosetti et al., "Management of Refractory Status Epilepticus in Adults: Still More Questions Than Answers"; Lancet Nuerol., vol. 10; pp. 922-930 (2011).
Shorvon et al., "The Treatment of Super-Refractory Status Epilepticus: A Critical Review of Available Therapies and a Clinical Treatment Protocol", Brain, vol. 134; pp. 2802-2818 (2011).
Botella, et al., "Neuroactive Steroids. 1. Positive Allosteric Modulators of the (gamma-Aminobutyric Acid)a Receptor: Structure—Activity Relationships of Heterocyclic Substitution at C-21" Journal of Medicinal Chemistry, vol. 58, pp. 3500-3511 (2015).
Wong et al., "Suspensions for intravenous (IV) injection: A review of development, preclinical and clinical aspects," Advanced Drug Delivery Reviews, vol. 60, pp. 939-954 (2008).
Moyne, et al., "Sterilization of injectable drugs solutions by irradiation" Radiation Physics and Chemistry, vol. 63; pp. 703-704 (2002).
ClinicalTrials.gov: "History of Changes for Study: NCT02358538, A Multicenter, Open-Label Proof-of-Concept Trial of Ganaxolone in Children with PCDH19 Female Pediatric Epilepsy and Other Rare Genetic Epilepsies," Publication Feb. 2015 and Jan. 16, 2017.
Press Release: "Marinus Pharmaceuticals Provides Business Update and Reports Second Quarter 2016 Financial Results," Published Aug. 9, 2016.
Lyden et al., "Effect of Ganaxolone in a Rodent Model of Cerebral Hematoma", American Heart Association, Inc. (2000); pp. 169-175.
Abstract and Corresponding Poster: "Ganaxolone Therapy Improves Interictal EEG and Seizure Control in Lennox Gastaut Syndrome in Patients with PCDH19 and CDKL5," Child Society for Neuroscience on Oct. 26, 2016.
Press Release: "Marinus Announces Positive Preliminary Data for Children with CDKL5 Genetic Disorder," Published Jan. 25, 2017.
Abstract and Corresponding Poster: "Ganaxolone Efficacy Observation in Patients with CDKL5 and PCDH19 with Lennox-Gastaut Syndrome Epileptic Encephalopathy: Seizure Reduction and EEG Findings," American Epilepsy Society, Abst. 1.180, Published Nov. 22, 2016.
Kerrigan et al., "Ganaxolone for treating intractable infantile spasms: a multicenter, open-label, add-on trial," Epilepsy Research, vol. 42, pp. 133-139 (2000).
Yawno et al., "Ganaxolone: A new treatment for neonatal seizures," Frontiers in Cellular Neuroscience, vol. 11, Article 246, pp. 1-7 (2017).
Liptakova, et al., "Effect of Ganaxolone on Flurothyl Seizures in Developing Rats," Epilepsia, 41(7):788-793 (2000).
International Search Report and Written Opinion from International PCT Application No. PCT/US2020/063648, dated Mar. 8, 2021, 16 pages.

GANAXOLONE FOR USE IN TREATING TUBEROUS SCLEROSIS COMPLEX

The present application claims the benefit of U.S. Provisional Application No. 62/944,549 filed on Dec. 6, 2019, the entire contents of which are incorporated herein by reference.

1. BACKGROUND

Tuberous sclerosis, also known as tuberous sclerosis complex (TSC), is a rare multisystem genetic disorder characterized by the growth of numerous noncancerous (benign) tumors in many parts of the body (Northrup et al., (2013), Pediatr Neurol., 49(4):243-254. These tumors can occur in the skin, brain, kidneys, and other organs, in many cases leading to significant health problems. Id.

Epilepsy is the most common neurological symptom in patients with TSC ("TSC-related epilepsy"), and significantly accounts for morbidity and mortality. Jülich and Sahin (2014), Pediatric Neurol., 50:290-296. Infantile spasms are the most common seizure type presenting in infancy and represent the first manifestation of epilepsy in 50% of patients. Id. In older children and adults, focal impaired awareness seizures (previously known as complex partial seizures) are the most common. Id. Other focal and generalized seizures may also occur. Id.

TSC-related epilepsy affects up to about 90% of patients, of which about 70% are treatment resistant (Portocarrero et al., (2018), An Bras Dermatol., 93(3):323-331). Further, there is a higher prevalence of intellectual disability, such as autism, mental retardation and mood disturbances, among patients with refractory epilepsy compared to those with control epilepsy, and disease manifestation continues over the lifetime of an affected individual. Id. The negative impact of epilepsy on the cognitive development, as well as on the quality of life makes seizure prevention and management an important goal in treating TSC (Vergeer et al., (2019), Epilepsia Open, 4:581-592).

There is no cure for this disorder. The first line therapy for TSC-associated infantile spasms is vigabatrin (Uliel-Sibony et al., (2020), Child's Nervous System, 36:2511-2517). However, vigabatrin is associated with severe adverse side-effects. Id. For example, it is associated with irreversible retinal damage in about 21-34% of patients. Other potential side-effects include brain abnormalities in the thalami, basal ganglia, brainstem tegmentum, and cerebellar dentate nuclei, hyperkinetic movement disorders, and acute encephalopathy. Id. Moreover, no other anti-seizure medications have dramatically reduced the severity or rate of TSC-related epilepsy.

Accordingly, there is a significant unmet need for effective therapies for treating TSC.

2. SUMMARY

This disclosure relates to methods for treating TSC and/or TSC-related epilepsy. As explained above, TSC and/TSC-related epilepsy is an extremely complicated and challenging condition to treat. In 70% of cases, patients are resistant to treatment and epilepsy is refractory. Refractory epilepsy is usually associated with significant behavioral as well as developmental consequences. As described and exemplified herein, the inventors believe that ganaxolone could provide effective therapy for TSC and/or TSC-related epilepsy.

Given the complexity and difficulties in treating TSC and TSC-related epilepsy, the inventors believed that a high dose of drug (e.g., ganaxolone) would be required for effective treatment. For example, in a clinical trial in adults with focal seizures, ganaxolone was administered at a daily dose of 1800 mg (administered as 900 mg twice a day), yet the clinical endpoint was not achieved. The inventors have now surprisingly discovered that administering ganaxolone at a lower daily dose but with more frequent administration can provide effective therapy for TSC and TSC-related epilepsy. Without wishing to be bound by any particular theory or mechanism, it is believed that more frequent administration of ganaxolone (e.g., three time a day) but at a lower daily dose than was used previously, improves drug exposure by maintaining a ganaxolone serum level (e.g., trough levels) above a threshold level for longer periods of time resulting in effective treatment. For example, administering oral ganaxolone three times daily (or more) with a total daily dose of no more than 1800 mg, or no more than 1700 mg, or no more than 1600 mg, or no more than 1500 mg, or no more than 63/mg/kg/day of ganaxolone can produce a plasma concentration of ganaxolone of at least about 100 ng/ml for approximately 70% or greater for a 24 hour-day, and provide effective seizure reduction. Also, less ganaxolone is typically required to achieve the increased trough concentration of ganaxolone using three time per day (or more frequent) administration, which is also beneficial for the subject under treatment. In fact, trough ganaxolone levels with twice a day dosing typically remained below 100 ng/ml over the 24 hour treatment period.

The inventors have also surprisingly discovered that a subpopulation of patients having TSC-related epilepsy have a low plasma concentration of allopregnanolone-sulfate (Allo-S) (e.g., less than 2,500 pg/ml) and may better respond to treatment with ganaxolone.

Accordingly, this disclosure relates to methods for effectively treating TSC and or TSC-related epilepsy. The methods disclosed herein comprise administering to a subject in need thereof a therapeutically effective amount of a neurosteroid, preferably ganaxolone, or a pharmaceutically acceptable salt thereof. Ganaxolone is preferably administered in an amount that will provide a trough ganaxolone level (e.g., a ganaxolone plasma concentration) of about 100 ng/ml or greater for approximately 70% or more for a 24 hour-day.

To achieve a ganaxolone plasma concentration of about 100 ng/ml or greater for approximately 70% or more over a 24 hour-day, ganaxolone can be administered three times daily (or more) at a maximum amount of about 1,800 mg per day. In subjects' that weigh less than 40 kg ganaxolone can be administered three times daily (or more) at a maximum amount of 63 mg/kg/day is Typically, up to about 1,500 mg per day of ganaxolone can produce a plasma concentration of about 100 ng/ml or greater for approximately 70% or more over a 24 hour-day when administered three times a day. Ganaxolone can be administered at a dose of about 500 mg three times a day. A skilled clinician will understand that the amount of ganaxolone administered three times a day (e.g., orally) can be adjusted to achieve the desired ganaxolone trough level so long as the total amount does not exceed the maximum daily dose of ganaxolone.

Preferably ganaxolone is administered orally (e.g., as an oral suspension or an oral capsule). Without being bound by theory, the inventors believe that three time dosing results in improved antiseizure activity (i.e., reduces seizure frequency and/or severity of seizures) because of increased plasma ganaxolone exposure. This is contrary to prior treatment protocols that teach administering ganaxolone at high dose (e.g., per day dose) to achieve therapeutic efficacy. For example, administering ganaxolone at a higher dose two times a day.

Administering ganaxolone at an amount to achieve a ganaxolone plasma concentration of at least about 100 ng/ml or greater for approximately about 70% or more for a period of 24 hours reduces the frequency of seizure and/or severity of seizure in the subject relative to baseline. Typically, a reduction in seizure frequency of at least about 20% or greater relative to baseline seizure frequency can be achieved. During treatment the plasma concentration of ganaxolone in the subject can be monitored and/or the subject can be monitored for seizure activity using EEG. If the subject appears to show signs of seizure (e.g., seizure reoccurrence), the amount of ganaxolone administered can be adjusted accordingly.

The methods disclosed herein are suitable to treat any form of seizure associated with TSC or TSC-related epilepsy. For example, but not limited to, infantile spasms, focal impaired awareness seizure, focal seizure, or generalized seizure.

It is an object of the disclosure to provide a treatment for tuberous sclerosis. It is an object of the disclosure to provide a treatment for tuberous sclerosis complex (TSC)-related epilepsy. It is a further object of the disclosure to provide a treatment for seizures associated with TSC-related epilepsy. It is another object of the disclosure to utilize ganaxolone's gamma-aminobutyric acid (GABA)-ergic mechanism of action to provide a therapeutic benefit to humans with TSC and TSC-related epilepsy.

In furtherance of the above objects and others, the disclosure is directed in part to a method of treating a human suffering from tuberous sclerosis comprising administering a therapeutically effective amount of a pharmaceutically acceptable pregnenolone neurosteroid to the human in an amount effective to alleviate or reduce one or more symptom(s) of tuberous sclerosis in the human. The pharmaceutically acceptable pregnenolone neurosteroid may be administered parenterally and/or orally in an amount of from about 1 mg/day to about 5000 mg/day. Humans particularly poised to receive a therapeutic benefit from administration of the pharmaceutically acceptable pregnenolone neurosteroid are humans having a low level of allopregnanolone-sulfate.

Allopregnanolone-sulfate plasma levels appear to positively correlate with allopregnanolone plasma levels and may qualitatively represent allopregnanolone levels in the brain. A low level of allopregnanolone-sulfate may therefore indicate a deficiency of allopregnanolone in the brain. A plasma allopregnanolone-sulfate level of about 2500 pg/ml or less is considered low, and may indicate a deficiency of endogenous neurosteroids in a human. The low level of allopregnanolone-sulfate may be 2400 pg/ml or less, 2300 pg/ml or less, 2200 pg/ml or less, 2100 pg/ml or less, 2000 pg/ml or less, 1900 pg/ml or less, 1800 pg/ml or less, 1700 pg/ml or less, 1600 pg/ml or less, 1500 pg/ml or less, 1400 pg/ml or less, 1300 pg/ml or less, 1200 pg/ml or less, 1100 pg/ml or less, 1000 pg/ml or less, 900 pg/ml or less, 850 pg/ml or less, 800 pg/ml or less, 750 pg/ml or less, 700 pg/ml or less, 650 pg/ml or less, 600 pg/ml or less, 550 pg/ml or less, 500 pg/ml or less, 450 pg/ml or less, 400 pg/ml or less, 350 pg/ml or less, 300 pg/ml or less, 250 pg/ml or less, 200 pg/ml or less, 150 pg/ml or less, 100 pg/ml or less, 90 pg/ml or less, 80 pg/ml or less, 70 pg/ml or less, 60 pg/ml or less, 50 pg/ml or less, 40 pg/ml or less, 30 pg/ml or less, 20 pg/ml or less, 15 pg/ml, 10 pg/ml or less, 9 pg/ml or less, 8 pg/ml or less, 7 pg/ml or less, 6 pg/ml or less, 5 pg/ml or less, 4 pg/ml or less, 3 pg/ml or less, 2 pg/ml or less, 1 pg/ml or less.

Because a deficiency of allopregnanolone in the brain may cause one or more symptoms of tuberous sclerosis, administration of a pharmaceutically acceptable pregnenolone neurosteroid in accordance with methods disclosed herein may correct this deficiency and, consequently, alleviate and/or reduce the severity and/or reduce the frequency of one or more symptom(s) of tuberous sclerosis in the methods disclosed herein. Symptoms of tuberous sclerosis that may be alleviated or reduce by administration of the pharmaceutically acceptable pregnenolone neurosteroid, include, but are not limited to, e.g., seizures, intellectual disability, developmental delay, behavioral problems, skin abnormalities, lung disease, and kidney disease. Seizures may include, e.g., focal motor seizures without impairment of consciousness or awareness, focal seizures with impairment of consciousness or awareness, focal seizures evolving to bilateral generalized convulsive seizures, tonic-clonic convulsive seizures, and generalized seizures with a motor component that are countable, including, for example, tonic-clonic, bilateral tonic, bilateral clonic, or atonic/drop seizures.

The disclosure is also directed to a method of treating a human suffering from tuberous sclerosis comprising administering a therapeutically effective amount of ganaxolone to the human in an amount effective to alleviate or reduce one or more symptom(s) of tuberous sclerosis in the human. Ganaxolone may be administered parenterally and/or orally. Humans particularly poised to receive a therapeutic benefit from administration of ganaxolone are humans having a low level of allopregnanolone-sulfate.

When ganaxolone is administered orally, the therapeutically effective amount of ganaxolone may be, e.g., from about 600 mg/day to about 2000 mg/day. In certain embodiments, the dose may be increased up to about 2100 mg/day, 2200 mg/day, 2300 mg/day, or higher, to provide an improved response over a lower dose, the limiting factors being increased side effects from the higher dose. Typically up about 1,500 mg/day or 1,800 mg/day of ganaxolone is administered. In certain embodiments, the dose may be decreased to about 550 mg/day, 500 mg/day, 450 mg/day, 300 mg/day, or lower than 300 mg/day, to alleviate or decrease severity of side effect(s) experienced by the human at a higher dose. Symptoms of tuberous sclerosis that may be alleviated and/or the frequency and/or severity of which may be reduced by administration of ganaxolone in accordance with the methods disclosed herein, include, e.g., seizures, intellectual disability, developmental delay, behavioral problems, skin abnormalities, lung disease, and kidney disease. Seizures may include, e.g., focal motor seizures without impairment of consciousness or awareness, focal seizures with impairment of consciousness or awareness, focal seizures evolving to bilateral generalized convulsive seizures, tonic-clonic convulsive seizures, and generalized seizures with a motor component that are countable, including, for example, tonic-clonic, bilateral tonic, bilateral clonic, or atonic/drop seizures.

The disclosure is also directed to a method of treating a human having TSC or TSC-related epilepsy, comprising chronically administering a pharmaceutically acceptable pregnenolone neurosteroid (e.g., ganaxolone) to the human in an amount effective to reduce a seizure frequency in the human, wherein the human has a low plasma level of an endogenous neurosteroid(s) (e.g., allopregnanolone-sulfate (Allo-S), as outlined above).

This disclosure is also directed to a method of treating a human with TSC or TSC-related epilepsy, the method comprising orally administering to the human a solid oral immediate release formulation comprising a pharmaceutically acceptable pregnenolone neurosteroid (e.g., ganaxolone) on a twice-a-day basis (e.g., every 10-13 hours), wherein the neurosteroid has a half-life of from about 18 hours to about 24 hours, the formulation releases not less than about 70% or about 80% of ganaxolone at 45 minutes of placing the formulation into a simulated gastrointestinal fluid (SGF and/or SIF), and the administration results in at least about a 35%, about a 40%, about a 45%, or about a 50% decrease in seizure frequency per 28 days in the human, as compared to the seizure frequency during a time period of 28 days before the first administration.

This disclosure is further directed to a method of treating a human with TSC or TSC-related epilepsy, the method comprising orally administering to the human a liquid oral immediate release formulation comprising a pharmaceutically acceptable pregnenolone neurosteroid (e.g., ganaxolone) three times a day (e.g., every 6 to 8 hours), wherein the neurosteroid has a half-life of from about 18 hours to about 24 hours, the formulation releases not less than about 70% or about 80% of ganaxolone at 45 minutes of placing the formulation into a simulated gastrointestinal fluid (SGF and/or SIF) and the administration results in at least about a 35%, about a 40%, about a 45%, or about a 50% decrease in seizure frequency per 28 days in the human, as compared to the seizure frequency during a time period of 28 days before the first administration.

This disclosure is also directed to a method for treating a human with a pregnenolone neurosteroid, wherein the human is suffering from TSC or TSC-related epilepsy, the method comprising the steps of: determining whether the human has a low level of endogenous neurosteroid (e.g., Allo-S) by obtaining or having obtained a biological sample (e.g., a sample of blood) from the human; and performing or having performed an assay on the biological sample to determine the plasma level of an endogenous neurosteroid(s) in the biological sample. A level of the endogenous neurosteroid of 2500 pg mL-1 or less, 2000 pg mL-1 or less, 1500 pg mL-1 or less, 1000 pg mL-1 or less, 900 pg mL-1 or less, 800 pg mL-1 or less, 700 pg mL-1 or less, 600 pg mL-1 or less, 500 pg mL-1 or less, 400 pg mL-1 or less, 300 pg mL-1 or less, 200 pg mL-1 or less, 100 pg mL-1 or less, 75 pg mL-1 or less, 50 pg mL-1 or less, or 25 pg mL-1 or less indicates that the human has the low level of endogenous steroid. A subject (e.g., a human) having low level of endogenous steroid (e.g., Allo-S) can be orally administered a pregnenolone neurosteroid (e.g., ganaxolone) at a dose of from 1 mg/kg/day to about 63 mg/kg/day, from about 2 mg/kg/day to about 63 mg/kg/day, from about 3 mg/kg/day to about 63 mg/kg/day, from about 4 mg/kg/day to about 63 mg/kg/day, from about 5 mg/kg/day to about 63 mg/kg/day, from about 6 mg/kg/day to about 63 mg/kg/day, or from about 7 mg/kg/day to about 63 mg/kg/day for at least one day in two or three divided doses.

In some of these embodiments, the level of endogenous neurosteroid of 2500 pg mL-1 or less, 2000 pg mL-1 or less, 1500 pg mL-1 or less, 1000 pg mL-1 or less, 900 pg mL-1 or less, 800 pg mL-1 or less, 700 pg mL-1 or less, 600 pg mL-1 or less, 500 pg mL-1 or less, 400 pg mL-1 or less, 300 pg mL-1 or less, 200 pg mL-1 or less, 100 pg mL-1 or less, 75 pg mL-1 or less, 50 pg mL-1 or less, or 25 pg mL-1 or less indicates that the administration of said ganaxolone is likely to reduce a seizure frequency in the patient, e.g., by 35%, or higher; about 40%, or higher; about 45%, or higher; or about 50%, or higher; after administration for 28 days, as compared to the seizure frequency during a time period of 28 days before the first administration. The endogenous neurosteroid may be selected from the group comprising or consisting of pregnanolone, pregnanolone-sulfate, 5-alphaDHP, allopregnanolone, allopregnanolone-S, pregnanolone, pregnanolone-S, DHEA, and combinations thereof; and the pregnenolone neurosteroid may, e.g., be selected from the group comprising or consisting of allopregnanolone, ganaxolone, alphaxalone, alphadolone, hydroxydione, minaxolone, pregnanolone, acebrochol, or tetrahydrocorticosterone, and pharmaceutically acceptable salts thereof. In some of these embodiments, the method further comprises communicating the results of the assay to the patient or a medical provider before or after the administration of the pregnenolone neurosteroid. Ganaxolone is the preferred pregnenolone neurosteroid.

This disclosure is also directed to a method for treating a human with ganaxolone, wherein the human is suffering from TSC or TSC-related epilepsy, the method comprising the steps of: determining whether the human has a level of allopregnanolone-sulfate (Allo-S) of 2500 pg mL-1 or less, and if the human has a level of allopregnanolone-sulfate of 2500 pg mL-1 or less, then orally administering ganaxolone to the human at a dose of from 1 mg/kg/day to about 63 mg/kg/day, from about 2 mg/kg/day to about 63 mg/kg/day, from about 3 mg/kg/day to about 63 mg/kg/day, from about 4 mg/kg/day to about 63 mg/kg/day, from about 5 mg/kg/day to about 63 mg/kg/day, from about 6 mg/kg/day to about 63 mg/kg/day, or from about 7 mg/kg/day to about 63 mg/kg/day for at least one day in two or three divided doses. In some of these embodiments, the level of allopregnanolone-sulfate of 2500 pg mL-1 or below indicates that the administration of said ganaxolone is likely to reduce a seizure frequency in the human, e.g., by at least about 35%, about 40%, about 45%, or about 50% after administration for 28 days, as compared to the seizure frequency during a time period of 28 days before the first administration.

This disclosure is further directed to a method for treating a human suffering from TSC or TSC-related epilepsy, the method comprising the steps of: determining whether the human has a level of allopregnanolone-sulfate of 2500 pg mL-1 or less, and if the human has a level of allopregnanolone-sulfate of 2500 pg mL-1 or less, then orally administering an endogenous neurosteroid (e.g., allopregnanolone, pregnanolone, etc.) or a synthetic neurosteroid (e.g., Co26749/WAY-141839, Co134444, Co177843, Sage-217 (3α-Hydroxy-3β-methyl-21-(4-cyano-1H-pyrazol-1'-yl)-19-nor-5β-pregnan-20-one), ganaxolone, etc.) to the human at a dose of from 1 mg/kg/day to about 200 mg/kg/day, from about 2 mg/kg/day to about 150 mg/kg/day, from about 3 mg/kg/day to about 100 mg/kg/day, from about 4 mg/kg/day to about 90 mg/kg/day, from about 5 mg/kg/day to about 80 mg/kg/day, from about 6 mg/kg/day to about 70 mg/kg/day, or from about 7 mg/kg/day to about 65 mg/kg/day for at least one day in two or three divided doses, and if the human has a level of allopregnanolone-sulfate above 2500 pg mL-1, refraining from administering the endogenous or the synthetic neurosteroid to the human and/or administering a different anti-convulsant agent. A different anti-convulsant agent may, e.g., be selected from the group consisting of benzodiazepines (e.g., clobazam, diazepam, clonazepam, midazolam, etc.), clorazepic acid, levetiracetam, felbamate, lamotrigine, a fatty acid derivative (e.g., valproic acid), a carboxamide derivative (rufinamide, carbamazepine, oxcarbazepine, etc.), an amino acid derivative (e.g., levocarnitine), a barbiturate (e.g., phenobarbital), or a combination of two or more of the foregoing agents. Any number of other anti-convulsant agents may be administered. A person skilled in the art will be familiar with anti-convulsant agents.

The disclosure is also directed to a method for treating a human suffering from TSC or TSC-related epilepsy, the method comprising the steps of: determining whether the human has a level of allopregnanolone-sulfate of 2500 pg mL-1 or less, and if the human has a level of allopregnanolone-sulfate of 2500 pg mL-1 or less, then orally administering ganaxolone to the human at a dose of from 1 mg/kg/day to about 63 mg/kg/day, from about 2 mg/kg/day to about 63 mg/kg/day, from about 3 mg/kg/day to about 63 mg/kg/day, from about 4 mg/kg/day to about 63 mg/kg/day, from about 5 mg/kg/day to about 63 mg/kg/day, from about 6 mg/kg/day to about 63 mg/kg/day, or from about 7 mg/kg/day to about 63 mg/kg/day for at least one day in two or three divided doses. In some of these embodiments, the level of allopregnanolone-sulfate of 2500 pg mL-1 or below indicates that the administration of said ganaxolone is likely to reduce a seizure frequency in the human, e.g., by at least about a 35%, about a 40%, about a 45%, or about a 50% after administration for 28 days, as compared to the seizure frequency during a time period of 28 days before the first administration.

This disclosure is further directed to a method for treating a human with TSC or TSC-related epilepsy, the method comprising the steps of: determining whether the human has a level of allopregnanolone of 200 pg mL-1 or less, and if the human has a level of allopregnanolone of 200 pg mL-1 or less, then orally administering ganaxolone to the human at a dose of from 1 mg/kg/day to about 80 mg/kg/day, from about 2 mg/kg/day to about 75 mg/kg/day, from about 3 mg/kg/day to about 70 mg/kg/day, from about 4 mg/kg/day to about 65 mg/kg/day, from about 5 mg/kg/day to about 63 mg/kg/day, from about 6 mg/kg/day to about 63 mg/kg/day, or from about 7 mg/kg/day to about 63 mg/kg/day for at least one day in two or three divided doses, and if the human has a level of allopregnanolone above 200 pg mL-1, refraining from administering ganaxolone to the human. In some of these embodiments, the level of allopregnanolone of 200 pg mL-1 or below indicates that the administration of said ganaxolone is likely to reduce a seizure frequency in the human, e.g., by at least about a 35%, about a 40%, about a 45%, or about a 50% after administration for 28 days, as compared to the seizure frequency during a time period of 28 days before the first administration.

The methods disclosed herein, may further comprise a step of measuring plasma levels of allopregnanolone in a human with TSC or TSC-related epilepsy. An allopregnanolone plasma level of about 200 pg/ml or less is a low level and may indicate that the human may have a deficiency of endogenous neurosteroids. Thus, in some embodiments, the low endogenous level of neurosteroid in the human may, e.g., be 200 pg/ml or less, 199 pg/ml or less, 198 pg/ml or less, 197 pg/ml or less, 196 pg/ml or less, 195 pg/ml or less, 194 pg/ml or less, 193 pg/ml or less, 192 pg/ml or less, 191 pg/ml or less, 190 pg/ml or less, 189 pg/ml or less, 188 pg/ml or less, 187 pg/ml or less, 186 pg/ml or less, 185 pg/ml or less, 184 pg/ml or less, 183 pg/ml or less, 182 pg/ml or less, 181 pg/ml or less, 180 pg/ml or less, 179 pg/ml or less, 178 pg/ml or less, 177 pg/ml or less, 176 pg/ml or less, 175 pg/ml or less, 174 pg/ml or less, 173 pg/ml or less, 172 pg/ml or less, 171 pg/ml or less, 170 pg/ml or less, 169 pg/ml or less, 168 pg/ml or less, 167 pg/ml or less, 166 pg/ml or less, 165 pg/ml or less, 164 pg/ml or less, 163 pg/ml or less, 162 pg/ml or less, 161 pg/ml or less, 160 pg/ml or less, 159 pg/ml or less, 158 pg/ml or less, 157 pg/ml or less, 156 pg/ml or less, 155 pg/ml or less, 154 pg/ml or less, 153 pg/ml or less, 152 pg/ml or less, 151 pg/ml or less, 150 pg/ml or less, 149 pg/ml or less, 148 pg/ml or less, 147 pg/ml or less, 146 pg/ml or less, 145 pg/ml or less, 144 pg/ml or less, 143 pg/ml or less, 142 pg/ml or less, 141 pg/ml or less, 140 pg/ml or less, 139 pg/ml or less, 138 pg/ml or less, 137 pg/ml or less, 136 pg/ml or less, 135 pg/ml or less, 134 pg/ml or less, 133 pg/ml or less, 132 pg/ml or less, 131 pg/ml or less, 130 pg/ml or less, 129 pg/ml or less, 128 pg/ml or less, 127 pg/ml or less, 126 pg/ml or less, 125 pg/ml or less, 124 pg/ml or less, 123 pg/ml or less, 122 pg/ml or less, 121 pg/ml or less, 120 pg/ml or less, 119 pg/ml or less, 118 pg/ml or less, 117 pg/ml or less, 116 pg/ml or less, 115 pg/ml or less, 114 pg/ml or less, 113 pg/ml or less, 112 pg/ml or less, 111 pg/ml or less, 110 pg/ml or less, 109 pg/ml or less, 108 pg/ml or less, 107 pg/ml or less, 106 pg/ml or less, 105 pg/ml or less, 104 pg/ml or less, 103 pg/ml or less, 102 pg/ml or less, 101 pg/ml or less, 100 pg/ml or less, 99 pg/ml or less, 98 pg/ml or less, 97 pg/ml or less, 96 pg/ml or less, 95 pg/ml or less, 94 pg/ml or less, 93 pg/ml or less, 92 pg/ml or less, 91 pg/ml or less, 90 pg/ml or less, 89 pg/ml or less, 88 pg/ml or less, 87 pg/ml or less, 86 pg/ml or less, 85 pg/ml or less, 84 pg/ml or less, 83 pg/ml or less, 82 pg/ml or less, 81 pg/ml or less, 80 pg/ml or less, 79 pg/ml or less, 78 pg/ml or less, 77 pg/ml or less, 76 pg/ml or less, 75 pg/ml or less, 74 pg/ml or less, 73 pg/ml or less, 72 pg/ml or less, 71 pg/ml or less, 70 pg/ml or less, 69 pg/ml or less, 68 pg/ml or less, 67 pg/ml or less, 66 pg/ml or less, 65 pg/ml or less, 64 pg/ml or less, 63 pg/ml or less, 62 pg/ml or less, 61 pg/ml or less, 60 pg/ml or less, 59 pg/ml or less, 58 pg/ml or less, 57 pg/ml or less, 56 pg/ml or less, 55 pg/ml or less, 54 pg/ml or less, 53 pg/ml or less, 52 pg/ml or less, 51 pg/ml or less, 50 pg/ml or less, 49 pg/ml or less, 48 pg/ml or less, 47 pg/ml or less, 46 pg/ml or less, 45 pg/ml or less, 44 pg/ml or less, 43 pg/ml or less, 42 pg/ml or less, 41 pg/ml or less, 40 pg/ml or less, 39 pg/ml or less, 38 pg/ml or less, 37 pg/ml or less, 36 pg/ml or less, 35 pg/ml or less, 34 pg/ml or less, 33 pg/ml or less, 32 pg/ml or less, 31 pg/ml or less, 30 pg/ml or less, 29 pg/ml or less, 28 pg/ml or less, 27 pg/ml or less, 26 pg/ml or less, 25 pg/ml or less, 24 pg/ml or less, 23 pg/ml or less, 22 pg/ml or less, 21 pg/ml or less, 20 pg/ml or less, 19 pg/ml or less, 18 pg/ml or less, 17 pg/ml or less, 16 pg/ml or less, 15 pg/ml or less, 14 pg/ml or less, 13 pg/ml or less, 12 pg/ml or less, 11 pg/ml or less, 10 pg/ml or less, 9 pg/ml or less, 8 pg/ml or less, 7 pg/ml or less, 6 pg/ml or less, 5 pg/ml or less, 4 pg/ml or less, 3 pg/ml or less, 2 pg/ml or less, 1 pg/ml or less, or 0 pg/ml.

This disclosure is further directed to a method for treating TSC or TSC-related epilepsy, the method comprising the steps of: determining whether the human has a level of allopregnanolone of 200 pg mL-1 or less, and if the human has a level of allopregnanolone of 200 pg mL-1 or less, then orally administering ganaxolone to the human at a dose of from 1 mg/kg/day to about 100 mg/kg/day, from about 2 mg/kg/day to about 80 mg/kg/day, from about 3 mg/kg/day to about 70 mg/kg/day, from about 4 mg/kg/day to about 65 mg/kg/day, from about 5 mg/kg/day to about 65 mg/kg/day, from about 6 mg/kg/day to about 65 mg/kg/day, or from about 7 mg/kg/day to about 65 mg/kg/day for at least one day This disclosure is also directed to a method of treating endogeneous neurosteroid deficiency in a human in need thereof comprising administering a pharmaceutically acceptable pregnenolone neurosteroid (e.g., ganaxolone) to the human at a dose of about 1800 mg, or less, per day, for at least 1 day, wherein the human has a genetic mutation in TSC1 gene, located on chromosome 9q34 and/or the TSC2 gene located on chromosome 16p13.3, and at one or more symptoms selected from the group consisting of hypomelanotic macules (≥3, at least 5-mm diameter), angiofibromas (≥3) or fibrous cephalic plaque, ungual fibromas (≥2), shagreen patch, multiple retinal hamartomas, cortical dysplasias, subependymal nodules, subependymal giant cell astrocytomas (≥2), cardiac rhabodomyoma, lymphangioleiomyomatosis (LAM), angiomyolipomas "Confetti" skin lesions, dental enamel pits (≥3), intraoral fibromas (≥2), retinal achromic patch, multiple renal cysts, nonrenal hamartomas.

In some of these embodiments, the pharmaceutically acceptable pregnenolone neurosteroid is ganaxolone and is administered orally in the amount of from about 200 mg/day to about 2500 mg/day, from about 200 mg/day to about 2250 mg/day, from about 200 mg/day to about 2000 mg/day, from about 300 mg/day to about 1800 mg/day, from about 400 mg/day to about 1800 mg/day, from about 450 mg/day to about 1800 mg/day, from about 675 mg/day to about 1800 mg/day, from about 900 mg/day to about 1800 mg/day, from about 1125 mg/day to about 1800 mg/day, from about 1350 mg/day to about 1800 mg/day, from about 1575 mg/day to about 1800 mg/day, or about 1800 mg/day, in two or three divided doses. In some embodiments, the human experiences seizures and administration of the pharmaceutically acceptable pregnenolone neurosteroid results in a 35%, or better (e.g., about a 40%, about 45%, about 50%, about 55%) reduction in mean seizure frequency per 28 days, as compared to the seizure frequency during a time period of 28 days before the first administration. In some embodiments, the improvement is 50% or more.

The methods disclosed herein may further comprise periodic measurements of plasma levels of the administered pharmaceutically acceptable pregnenolone neurosteroid(s) (e.g., ganaxolone) and/or concomitant AED medication(s), if any, and/or allopregnanolone (3α-hydroxy-5α-pregnan-20-one) and/or related endogenous CNS-active steroids. In some embodiments, the plasma levels of liver enzymes (AST, ALT and ALK Phos) are also measured before, during or after initiation of treatment with the pharmaceutically acceptable pregnenolone neurosteroid. The plasma levels may, e.g., be measured weekly, every 2 weeks, every 3 weeks, every 4 weeks, every 5 weeks, every 6 weeks, every 7 weeks, every 8 weeks, every 9 weeks, every 10 weeks, every 11 week, or every 12 weeks.

The pregnenolone neurosteroid (e.g., ganaxolone) may be administered orally or parenterally in the methods described herein on a chronic basis. In certain preferred embodiments, the pregnenolone neurosteroid is ganaxolone and is administered as an oral suspension or an oral solid dosage form (e.g., oral capsule) at a dose of up to a total of 63 mg/kg/day, and ganaxolone is preferably administered up to a maximum amount of 1800 mg/day. Preferably, ganaxolone is administered chronically, e.g., for as long as the patient receives a therapeutic benefit from the treatment without untoward side effects requiring discontinuation of treatment. In certain embodiments, ganaxolone is administered for at least one day, at least 2 days, at least 3 days, 2 weeks, at least 3 weeks, at least 4 weeks, at least 5 weeks, at least 6 weeks, at least 7 weeks, at least 8 weeks, at least 9 weeks, at least 10 weeks, at least 11 weeks or at least 12 weeks. In some embodiments, ganaxolone may be administered for a time period of 2 weeks to 100 years, or for life of the human.

When the pregnenolone neurosteroid is administered in an oral suspension, it may be administered, e.g., anywhere from one to three times per day. In certain preferred embodiments, when the pregnenolone neurosteroid (e.g., ganaxolone) is orally administered, it may be administered with food (for better absorption) or without food. When the pregnenolone neurosteroid is administered in an oral tablet or capsule, it may be administered, e.g., anywhere from one to four times per day. When the pregnenolone neurosteroid is administered parenterally, it may be administered, e.g., anywhere from one to about three times per day, or as needed.

The disclosure is also directed in part to immediate release formulations comprising particles comprising (i) a pregnenolone neurosteroid (e.g., ganaxolone) and (ii) one or more pharmaceutically acceptable excipient(s) (e.g., oral suspensions, tablets or capsules), wherein the particles have a particle size that ensures an absence of agglomeration following dispersal in simulated gastrointestinal fluids (SGF and/or SIF) and does not change upon storage of the formulation at 25° C./60% RH for 1 month for use in TSC and/or TSC-related epilepsy. In the preferred embodiments, the formulation releases not less than about 70% or about 80% of the pregnenolone neurosteroid at 45 minutes of placing the formulation into 500 ml of a dissolution medium (e.g., 5% SLS in SGF (Simulated Gastric Fluid) and/or 5% SLS in SIF (Simulated Intestinal Fluid)) at 37° C.+0.5° C. in USP Apparatus 1 (Basket) at 100 rpm, and, after a single dose and/or multiple dose administrations, provides a plasma level of the pregnenolone neurosteroid of from about 55 ng/mL, about 60 ng/ml or about 65 ng/ml to a plasma level of the pregnenolone neurosteroid of from about 240 ng/ml to 400 ng/ml (e.g., 262 ng/mL) for a time period of at least about 6 hours, about 7 hours, about 8 hours, about 9 hours, about 10 hours, or about 12 hours. In some of these embodiments, the volume weighted median diameter of the particles is from about 250 nm to about 450 nm (e.g., about 332 nm). In some of the embodiments, the particles have a D(10) particle size of from about 200 nm to about 220 nm, a D(50) particle size of from about 250 nm to about 450 nm and a D(90) particle size of from about 480 nm to about 700 nm, and the formulation is free from cyclodextrins, including sulfoalkyl ether cyclodextrins and modified forms thereof, and is for treating a TSC-related epilepsy.

This disclosure is also directed in part to an oral immediate release formulation comprising particles comprising (i) ganaxolone and (ii) one or more pharmaceutically acceptable excipient(s) (e.g., oral suspensions, tablets or capsules) for use in TSC and/or TSC-related epilepsy, wherein the particles have a mean particle size of about 0.3 micron (i.e., volume weighted median diameter (D50) of about 0.3 micron); the particle size does not change upon storage of the formulation at 25° C./60% RH for 1 month; the formulation releases not less than about 70% or about 80% of ganaxolone at 45 minutes of placing the formulation into 500 ml of a dissolution medium (e.g., 5% SLS in SGF (Simulated Gastric Fluid) and/or 5% SLS in SIF (Simulated Intestinal Fluid)) at 37° C.+0.5° C. in USP Apparatus 1 (Basket) at 100 rpm; the formulation provides, after a single dose and/or multiple doses, a plasma level of ganaxolone of from about 55 ng/mL, about 60 ng/ml or about 65 ng/ml to a plasma level of from about 240 ng/ml to 400 ng/ml (e.g., 262 ng/mL) for at least 6 hours to 12 hours after administration, and is for treatment of TSC or TSC-related epilepsy. The plasma level of ganaxolone of from about 55 ng/mL, about 60 ng/ml or about 65 ng/ml to a plasma level of from about 240 ng/ml to 400 ng/ml (e.g., 262 ng/mL) may be provided after a fasting and/or fed administration of the formulation.

In some of these embodiments, the mean particle size of about 0.3 micron is critical for providing the dissolution of not less than about 70% or about 80% of the pregnenolone neurosteroid at 45 minutes of placing the formulation into a simulated gastrointestinal fluid (SGF and/or SIF) and the plasma level of the pregnenolone neurosteroid of from about 55 ng/mL, about 60 ng/ml or about 65 ng/ml to a plasma level of the pregnenolone neurosteroid of from about 240 ng/ml to 400 ng/ml (e.g., 262 ng/mL) for the time period of at least about 6 hours, about 7 hours, about 8 hours, about 9 hours, about 10 hours, or about 12 hours.

The disclosure is also directed in part to an immediate release formulations comprising particles comprising (i) ganaxolone and (ii) one or more pharmaceutically acceptable excipient(s) (e.g., oral suspensions, tablets or capsules) for use in TSC and/or TSC-related epilepsy, wherein the particles have a mean particle size of about 0.3 micron; the particle size does not change upon storage of the formulation at 25° C./60% RH for 2 months and/or 3 months and/or 4 months; the formulation releases not less than 80% of ganaxolone at 45 minutes of placing the formulation into 500 ml of a dissolution medium (e.g., 5% SLS in SGF (Simulated Gastric Fluid) and/or 5% SLS in SIF (Simulated Intestinal Fluid)) at 37° C.+0.5° C. in USP Apparatus 1 (Basket) at 100 rpm); the formulation provides a plasma level of ganaxolone of from about 55 ng/mL, about 60 ng/ml or about 65 ng/ml to a plasma level of from about 240 ng/ml to 400 ng/ml (e.g., 262 ng/mL) for at least 6 hours to 12 hours after administration.

3. BRIEF DESCRIPTION OF THE DRAWINGS

FIG. 1 depicts baseline endogenous allopregnenolone-sulfate ("Allo-S") levels in female patients with PCDH19-related epilepsy stratified by responder vs. non-responder. When stratifying patients with allopregnanolone-sulfate (Allo-S) levels <2.5 ng mL-1, a 50% median reduction in seizure frequency (n=7) compared to baseline was observed. This analysis was conducted retrospectively in a small, open label cohort. Nevertheless, the 1.5-2 orders of magnitude difference in allopregnanolone-sulfate levels between responders and non-responders suggests that plasma levels of allopregnanolone-sulfate may be used to predict efficacy of a pharmaceutically acceptable pregnenolone neurosteroids. These data provide preliminary evidence that a plasma level of allopregnanolone-sulfate may be used as a predictive biomarker to prospectively identify patient(s) that may experience an enhanced treatment effect from ganaxolone.

FIG. 2 depicts allopregnanolone-sulfate (Allo-S) levels in patients with TSC versus Control, based on plasma samples from the Biosample Repository. The objective was to quantify endogenous neurosteroid levels using our proprietary validated analytical methods (LC/MS/MS) and compare the levels to healthy (unaffected) age-matched control samples. Plasma samples from TSC patients with epilepsy demonstrated a trend towards reduced Allo-S levels (n=47, median 1.8 ng mL-1) when compared to controls (n=60, median 4.1 ngmL-1). This finding was enhanced when isolating only patients/subjects aged 1-14 years of age (n=28 TSC, n=28 control). Patients/subjects included 29 females, 18 males. Female median age was 15 year old (range 2-27 year old). Male median age was 10.5 years old (range 2-33 year old). Fluctuations in neurosteroid levels post-puberty may confound the analysis in all patients.

4. DETAILED DESCRIPTION

Figure 1:
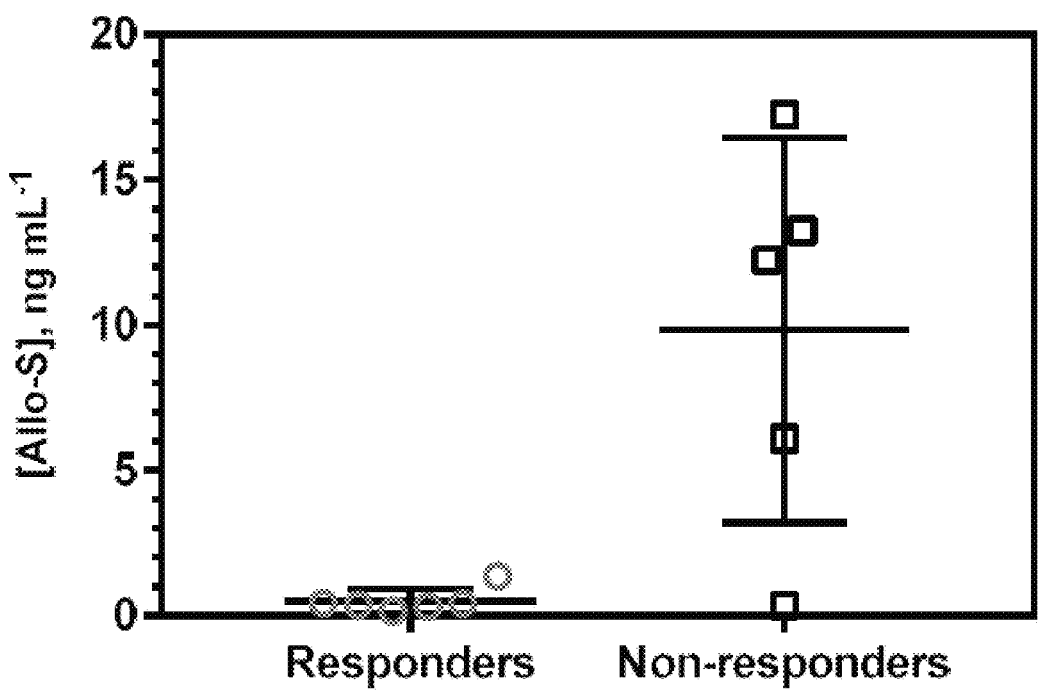

Effectively treating TSC and/or TSC-related epilepsy has been challenging and conventional treatment protocols are not effective in many patients. Indeed, about 70% of patients are resistant to treatment and epilepsy is refractory. The majority of seizures start within the first 12 months of life and as such there is a high prevalence of intellectual disability. Seizure control can reduce such developmental consequences. As such, there is a dire need for improved methods for treating TSC and/or TSC-related epilepsy.

This disclosure relates to new methods for treating SE. As exemplified and described herein, treatment according to the methods provides a reduction in seizure frequency and/or suppresses seizure in TSC-related epilepsy. The methods can be used to treat any form of TSC-related epilepsy. For example, but are not limited to, infantile spasms, focal motor seizures without impairment of consciousness or awareness, focal seizures with impairment of consciousness or awareness, focal seizures evolving to bilateral, tonic-clonic convulsive seizures, and generalized seizures motor seizures including tonic-clonic, bilateral tonic, bilateral clonic, atonic/drop seizures that are countable, myoclonic seizures, or epileptic seizures.

The method described herein comprises administering to a subject a therapeutically effective amount of a neurosteroid. Ganaxolone is a preferable neurosteroid.

The methods described herein can further comprise administering ganaxolone at a therapeutically effective amount to achieve a plasma concentration of ganaxolone of 100 ng/ml or higher for approximately 70% or more for a 24 hour-day. This can be achieved by administering ganaxolone at least three times a day. Three times a day is preferable, although in some instances it may be appropriate to administer ganaxolone more than three times a day to achieve the desired trough concentration of ganaxolone. A plasma concentration of at least about 100 ng/ml or higher for approximately 70% or more of a 24 hour-day results in improved seizure reduction and/or suppression of seizure. For example, a seizure reduction of at least 20% or greater relative to baseline seizure frequency can be achieved. A lower maximum dose of ganaxolone administered over three times daily dosing can achieve the desired trough concentration of ganaxolone. Typically, a maximum daily dose of about 1,800 mg, and preferably 1,500 mg of ganaxolone is administered. The maximum daily dose of ganaxolone is administered at the same or varying doses across at least three intervals in a 24 hour-day.

The methods disclosed herein can further comprise determining whether a patient having TSC or TSC-related epilepsy will benefit from treatment with a neurosteroid (e.g., ganaxolone). A subpopulation of patients having TSC-related epilepsy have a low plasma concentration of Allo-S (e.g., less than 2,500 pg/ml) and may better response to treatment with ganaxolone. The methods described herein can comprise measuring the level of an endogenous neurosteroid of the subject prior to commencing treatment with a neurosteroid (e.g., a ganaxolone). A low level of endogenous neurosteroid can indicate that the subject will respond to treatment with a neurosteroid. Once it is has been determined that the subject has a low endogenous neurosteroid level, a therapeutically effective amount of a neurosteroid can be administered to the subject.

Additional description of the method and guidance for the practice of the method are provided herein. For ease of presentation, further details and guidance are provided with respect to a preferred aspect using ganaxolone. It is intended that the further details and guidance also relate to treatment with other neurosteroids.

I. Definitions

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. Thus compositions slightly outside the cited ranges are also encompassed by the scope of the present claims.

An "active agent" is any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers in pure form and mixtures thereof are encompassed. In addition, compounds with carbon-carbon double bonds may occur in Z- and E-forms, with all isomeric forms of the compounds being included in the present invention. In these situations, the single enantiomers, i.e. optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The term "endogenous neurosteroid" means a steroid produced within the brain and capable of modulating neuronal excitability by interaction with neuronal membrane receptors and ion channels, principally GABA-A receptors, and includes, e.g., pregnane neurosteroids (e.g., allopregnanolone, allotetrahydrodeoxycorticosterone, etc.), androstane neurosteroids (e.g., androstanediol, etiocholanone, etc.), and sulfated neurosteroids (e.g., pregnanolone sulfate, dehydroepiandrosterone sulfate (DHEAS)).

The term "pregnenolone neurosteroid" means an endogenous or exogenous steroid capable of modulating neuronal excitability by interaction with neuronal membrane receptors and ion channels, principally GABA-A receptors, and encompasses, e.g., endogenous neurosteroids and synthetic neurosteroids synthesized or derived from pregnenolone in vitro and in vivo.

The term "biomarker" means a serum or plasma level of a neurosteroid that differentiates a drug responder from a non-responder.

The terms "serum" and "plasma" as disclosed herein may be used interchangeably.

The terms "comprising," "including," and "containing" are non-limiting. Other non-recited elements may be present in embodiments claimed by these transitional phrases. Where "comprising," "containing," or "including" are used as transitional phrases other elements may be included and still form an embodiment within the scope of the claim. The open-ended transitional phrase "comprising" encompasses the intermediate transitional phrase "consisting essentially of" and the close-ended phrase "consisting of."

A "bolus dose" is a relatively large dose of medication administered in a short period, for example within 1 to 30 minutes.

"$C_{max}$" is the concentration of an active agent in the plasma at the point of maximum concentration.

"Ganaxolone" is also known as 3α-hydroxy-5α-pregnan-20-one, and is alternatively referred to as "GNX" in this document.

"Infusion" administration is a non-oral administration, typically intravenous though other non-oral routes such as epidural administration are included in some embodiments. Infusion administration occurs over a longer period than a bolus administration, for example over a period of at least 15 minutes, at least 30 minutes, at least 1 hour, at least 2 hours, at least 3 hours, or at least 4 hours.

A "patient" is a human or non-human animal in need of medical treatment. Medical treatment includes treatment of an existing condition, such as a disorder or injury. In certain embodiments treatment also includes prophylactic or preventative treatment, or diagnostic treatment.

A "child" means a human from 1 day to 18 years old (e.g., from 1 day to 15 years old), including 18 years old.

An "adult" means a human that is older than 18 years old.

"Pharmaceutical compositions" are compositions comprising at least one active agent, such as a compound or salt, solvate, or hydrate of Formula (I), and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as a seizure disorder.

"Povidone" also known as polyvidone and polyvinylpyrrolidone (PVP) is a water soluble polymer made from the monomer, N-vinylpyrrolidone. Plasdone C-12 and C-17 are pharmaceutical grade homopolymers of N-vinylpyrrolidone. Plasdone C-12 has a K value of 10-2-13.8 and nominal molecular weight of 4000 d. Plasdone C-17 has a K-value of 15.5-17.5 and nominal molecular weight of 10,000 d.

"Sterilize" means to inactivate substantially all biological contaminates in a sample, formulation, or product. A 1-million fold reduction in the bioburden is also considered "sterilized" for most pharmaceutical applications.

The term "reduce" seizure or seizure activity refer to the detectable decrease in the frequency, severity and/or duration of seizures. A reduction in the frequency, severity and/or duration of seizures can be measured by self-assessment (e.g., by reporting of the patient) or by a trained clinical observer. Determination of a reduction of the frequency, severity and/or duration of seizures can be made by comparing patient status before and after treatment.

A "therapeutically effective amount" or "effective amount" is that amount of a pharmaceutical agent to achieve a pharmacological effect. The term "therapeutically effective amount" includes, for example, a prophylactically effective amount. An "effective amount" of neurosteroid is an amount needed to achieve a desired pharmacologic effect or therapeutic improvement without undue adverse side effects. The effective amount of neurosteroid will be selected by those skilled in the art depending on the particular patient and the disease. It is understood that "an effective amount" or "a therapeutically effective amount" can vary from subject to subject, due to variation in metabolism of neurosteroid, age, weight, general condition of the subject, the condition being treated, the severity of the condition being treated, and the judgment of the prescribing physician.

"Treat" or "treatment" refers to any treatment of a disorder or disease, such as inhibiting the disorder or disease, e.g., arresting the development of the disorder or disease, relieving the disorder or disease, causing regression of the disorder or disease, relieving a condition caused by the disease or disorder, or reducing the symptoms of the disease or disorder.

"Alkyl" is a branched or straight chain saturated aliphatic hydrocarbon group, having the specified number of carbon atoms, generally from 1 to about 8 carbon atoms. The term $C_1$-$C_6$-alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$-alkyl, $C_1$-$C_4$-alkyl, and $C_1$-$C_2$-alkyl. Examples of alkyl include, but are not limited to, methyl, ethyl, n-propyl, isopropyl, n-butyl, 3-methylbutyl, t-butyl, n-pentyl, and sec-pentyl.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Aryl groups include, for example, phenyl, naphthyl, including 1-naphthyl, 2-naphthyl, and bi-phenyl. An "arylalkyl" substituent group is an aryl group as defined herein, attached to the group it substitutes via an alkylene linker. The alkylene is an alkyl group as described herein except that it is bivalent.

"Cycloalkyl" is a saturated hydrocarbon ring group, having the specified number of carbon atoms. Monocyclic cycloalkyl groups typically have from 3 to about 8 carbon ring atoms or from 3 to 6 (3, 4, 5, or 6) carbon ring atoms. Cycloalkyl substituents may be pendant from a substituted nitrogen, oxygen, or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

A "heteroalkyl" group is an alkyl group as described with at least one carbon replaced by a heteroatom, e.g. N, O, or S.

The term "substituted" as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, e.g., halogen; cyano; —OH; oxo; —NH$_2$; nitro; azido; alkanoyl (such as a $C_2$-$C_6$ alkanoyl group); C(O)NH$_2$; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; mono- or dialkylamino groups including groups having alkyl groups from 1 to about 6 carbon atoms; mono- or dialkylaminocarbonyl groups (i.e. alkylNHCO- or (alkyl1)(alkyl2)NCO—) having alkyl groups from about 1 to about 6 carbon atoms; aryl having 6 or more carbons.

II. Tuberous Sclerosis Complex

Tuberous Sclerosis Complex (TSC) is a multi-system disorder of embryonal cortical development which can impact many organs through the overgrowth of benign tumors known as hamartomas. A combination of symptoms may include seizures, intellectual disability, developmental delay, behavioral problems, skin abnormalities, lung disease, and kidney disease. While the disease phenotype of TSC can be extremely variable, neurologic manifestations such as epilepsy can be seen in up to 90% of TSC patients (Krueger et al., 2013). The condition is caused by inherited mutations in either the TSC1 gene, located on chromosome 9q34, or the TSC2 gene located on chromosome 16p13.3. TSC occurs with a frequency of 1:6,000 and a mutation is found in 85% of patients (Mich & Sahin, 2014). The gene products hamartin (TSC1) and tuberin (TSC2) form a regulatory complex responsible for limiting the activity of mammalian target of rapamycin complex 1 (mTORC1), an important intracellular regulator of growth and metabolism via its inhibition of the small GTPase Ras homolog enriched in brain (Rheb) (Krueger et al., 2013). Everolimus, an mTOR inhibitor, has been shown to decrease seizures (French et al, 2016; Mizuguchi et al., 2019).

TSC is one of the most common genetic causes of epilepsy, with seizure semiology that varies by age of onset (Jülich & Sahin, 2014). Effective treatment options include the use of adrenocorticotropic hormone (ACTH) which include a possible mechanism that aligns with ganaxolone use. ACTH has been shown to have stimulatory effects on deoxycorticosterone (DOC) which undergoes further synthesis to various neurosteroids. In specific, ACTH has been shown to rapidly increase endogenous plasma and brain levels of allopregnanolone which possibly could further explain the beneficial effect on IS.

Infantile spasms ("IS") are the most common seizure type presenting in infancy and represent the first manifestation of epilepsy in 50% of patients. In older children and adults, focal impaired awareness seizures (previously known as complex partial seizures) are the most common. Other focal and generalized seizures may also occur, with over 30% of patients developing treatment-refractory epilepsy (Jülich & Sahin, 2014). While seizures have typically been ascribed to tubers and the surrounding cortex, epilepsy in TSC can be considered multifactorial in origin as seizures can originate in other brain areas or can occur in TSC patients without tubers (Jülich & Sahin, 2014).

Clinical diagnosis of definite TSC which includes two major features or one major feature with ≥2 minor features from Table 7 below.

TABLE 7

| Major features | Minor features |
|---|---|
| 1. Hypomelanotic macules (≥3, at least 5-mm diameter) | 1. "Confetti" skin lesions |
| 2. Angiofibromas (≥3) or fibrous cephalic plaque | 2. Dental enamel pits (≥3) |
| | 3. Intraoral fibromas (≥2) |
| | 4. Retinal achromic patch |
| 3. Ungual fibromas (≥2) | 5. Multiple renal cysts |
| 4. Shagreen patch | 6. Nonrenal hamartomas |
| 5. Multiple retinal hamartomas | |
| 6. Cortical dysplasias* | |
| 7. Subependymal nodules | |
| 8. Subependymal giant cell astrocytomas | |
| 9. Cardiac rhabdomyoma | |
| 10. Lymphangioleiomyomatosis (LAM)** | |
| 11. Angiomyolipomas (≥2)** | |

*Includes tubers and cerebral white matter radial migration lines
**A combination of the two major clinical features (LAM and angiomyolipomas) without other features that does not meet criteria for a definite diagnosis.

γ-Aminobutyric acid (GABA) appears to play a central role in the development of TSC-related epilepsy, possibly due to altered expression of endogenous $GABA_A$ receptor modulators (di Michele et al., 2003).

There is evidence supporting a deficiency of the neuroactive steroid, 3α, 5α-tetrahydroprogesterone (THP), or allopregnanolone, as a contributor to epileptogenesis in TSC. Allopregnanolone is a positive modulator of the GABAA receptor and has been shown to have antiepileptic effects in experimental animals and humans. There is a decrease in allopregnanolone relative to its functional GABAA antagonist, 3β-THP, in patients with TSC-related epilepsy but not in TSC patients without epilepsy or in controls (di Michele et al., 2003). This reduced ratio could alter neuronal excitability mediated by GABAA receptors, leading to the development of epilepsy. The role of GABAA receptor mediation is also supported by the greater efficacy of vigabatrin, a specific and irreversible inhibitor of GABA-aminotransferase, in seizures due to TSC relative to other epilepsies (di Michele et al., 2003).

TSC patients with epilepsy have reduced levels of endogenous neurosteroids, particularly Allo, similar to previous reports in PCDH19. About 25% of all TSC patients have allopregnenalone-sulfate plasma level of less than 6 ng/ml.

Neuroactive steroids with anticonvulsant properties may have utility in the treatment of TSC and TSC-related epilepsy. Neuroactive steroids with anticonvulsant properties may increase GABAA-mediated signaling and improve not only seizure control, but may also ameliorate the behavioral abnormalities in individuals with TSC and TSC-related epilepsy.

Upregulation of the TSC-mTOR pathway leads to an increased inflammatory response with evidence of increased pro-inflammatory toll like receptor 4 (TLR4) signaling. Neurosteroids, including Allo, have been shown to act as inhibitors of various neuroinflammatory pathways including TLR4 expanding the mechanism of action of these compounds beyond positively modulating GABAA receptors.

III. Neurosteroids

Endogenous neurosteroids play a critical role in maintaining homeostasis of brain activity. Neurosteroids have the ability to enact brain changes rapidly in response to changes in the brain environment. Neurosteroids are devoid of interactions with classical steroid hormone receptors that regulate gene transcription; they modulate brain excitability primarily by interaction with neuronal membrane receptors and ion channels.

Neurosteroids can be positive or negative regulators of the $GABA_A$ receptor function, depending on the chemical structure of the steroid molecule (Pinna and Rasmussen, 2014, Reddy, 2003). The $GABA_A$ receptor mediates the lion's share of synaptic inhibition in the CNS. Structurally, $GABA_A$ receptors are hetero-pentamers of 5 protein subunits to form the chloride ion channels. There are 7 different classes of subunits, some of which have multiple homologous variants (α1-6, β1-3, γ1-3, σ1-3, δ, ε, θ); most $GABA_A$ receptors are composed of α, β and γ or δ subunits. The neurotransmitter GABA activates the opening of chloride ion channels, permitting chloride ion influx and ensuing hyperpolarization. $GABA_A$ receptors prevent action potential generation by swerving the depolarization produced by excitatory neurotransmission. There are 2 types of inhibitory neurotransmission mediated via $GABA_A$ receptors: synaptic (phasic) and extrasynaptic (tonic) inhibition. Neurosteroids modulate both synaptic and extrasynaptic $GABA_A$ receptors, and thereby potentiate both phasic and tonic currents. Phasic inhibition results from the activation of γ2-containing receptors at the synapse by intermittent release of millimolar concentrations of GABA from presynaptic GABA-ergic inter-neurons' axon terminals. Tonic inhibition, in contrast, is mediated by the continuous activation of δ-containing extra-synaptic receptors outside of the synaptic cleft by low levels of ambient GABA which escaped reuptake by GABA transporters. Tonic inhibition plays a unique role in controlling hippocampus excitability by setting a baseline of excitability (Reddy 2010).

Neurosteroids such as ganaxolone are potent positive allosteric modulators of $GABA_A$ receptors (Akk et al, 2009). The first observation that neurosteroids enhance GABA-evoked responses that are mediated by $GABA_A$ receptors was reported in 1984 with alphaxolone (Harrison and Simmonds, 1984). This modulating effect of neurosteroids occurs by binding to discrete sites on the $GABA_A$ receptor that are located within the transmembrane domains of the α- and β-subunits (Hosier et al, 2007; Hosier et al, 2009). The binding sites for neurosteroids are distinct from that of the GABA, benzodiazepine, and barbiturate. Although the exact locations of neurosteroid binding sites are currently unknown, it has been shown that a highly conserved glutamine at position 241 in the M1 domain of the α-subunit plays a key role in neurosteroid modulation (Hosie et al, 2009). In addition to the binding sites, there are also differences between neurosteroids and benzodiazepines in their respective interactions with $GABA_A$ receptors. While neurosteroids modulate most $GABA_A$ receptor isoforms, benzodiazepines only act on $GABA_A$ receptors that contain γ2-subunits and do not contain α4- or α6-subunits (Lambert et al, 2003; Reddy, 2010). The specific α-subunit may influence neurosteroid efficacy, whereas the γ-subunit type may affect both the efficacy and potency for neurosteroid modulation of $GABA_A$ receptors (Lambert et al, 2003).

Recent studies have indicated the existence of at least 3 neurosteroid binding sites on the $GABA_A$ receptor: 1 for allosteric enhancement of GABA-evoked currents by allopregnanolone, 1 for direct activation by allopregnanolone, and 1 for antagonist action of sulfated neurosteroids such as pregnanolone sulfate, at low (nM) concentrations (Lambert et al, 2003; Hosie et al, 2007). Neurosteroid enhancement of $GABA_A$ receptor chloride currents occurs through increases in both the channel open frequency and channel open duration (Reddy, 2010). Thus, neurosteroids greatly enhance the probability of $GABA_A$ receptor chloride channel opening that allows a massive chloride ion influx, thereby promoting augmentation of inhibitory GABA-ergic transmission. These effects occur at physiological concentrations of neurosteroids. Thus, endogenous neurosteroid levels continuously modulate the function of $GABA_A$ receptors (Reddy, 2010).

The extra-synaptic δ-subunit containing $GABA_A$ receptors exhibit increased sensitivity to neurosteroids, suggesting a key modulatory role in tonic inhibition (Wohlfarth et al., 2002). $GABA_A$ receptors that contain the δ subunit are more sensitive to neurosteroid-induced potentiation of GABA responses (Stell et al, 2003). Mice lacking δ subunit show drastically reduced sensitivity to neurosteroids (Mihalek et al, 1999). The δ-subunit does not contribute to the neurosteroid binding site, but appears to confer enhanced transduction of neurosteroid action after the neurosteroid has bound to the receptor. $GABA_A$ receptors containing the δ-subunit have a low degree of desensitisation, facilitating the mediating tonic $GABA_A$ receptor currents that are activated by ambient concentrations of GABA in the extracellular space. Tonic $GABA_A$ receptor current causes a steady inhibition of neurons and reduces their excitability. GABA is a relatively low efficacy agonist of δ-containing $GABA_A$ receptors even though it binds with high affinity (Glykys and Mody, 2007). Thus, neurosteroids can markedly enhance the current generated by δ-containing $GABA_A$ receptors even in the presence of saturating GABA concentrations. During neuronal activity, there is expected to be substantial release of GABA from active GABA-ergic interneurons that can interact with perisynaptic and extrasynaptic δ-subunit containing $GABA_A$ receptors. Overall, the robust effect of neurosteroids is likely to be due to their action on both synaptic and perisynaptic/extrasynaptic $GABA_A$ receptors (Reddy, 2010).

Pregnane neurosteroids and pregnenolone neurosteroid are a class of compounds useful as anesthetics, sedatives, hypnotics, anxiolytics, anti-depressants, anti-tremor, a treatment for autistic behavior, and anticonvulsants. These compounds are marked by very low aqueous solubility, which limits their formulation options. A nanoparticulate formulations of pregnane and pregnenolone neurosteroids that are bioavailable orally and parenterally can be used.

Injectable formulations of pregnane neurosteroids and pregnenolone neurosteroid are particularly desirable as these compounds are used for clinical indications for which oral administration is precluded, such as anesthesia and particularly for the emergency treatment of active seizures.

The disclosure includes injectable nanoparticle neurosteroid formulations.

The pregnane neurosteroid and pregnenolone neurosteroid of the present invention may each be a compound of Formula IA:

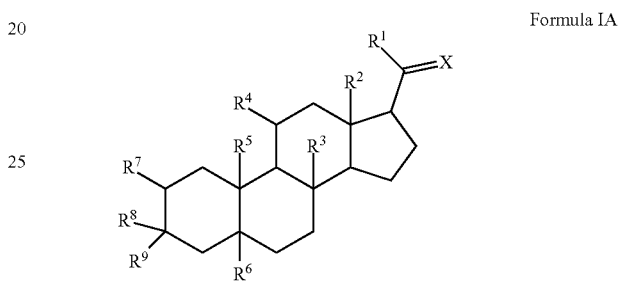

Formula IA or a pharmaceutically acceptable salt thereof, wherein:
X is O, S, or $NR^{10}$;
$R^1$ is hydrogen, hydroxyl, —$CH_2A$, optionally substituted alkyl, optionally substituted heteroalkyl, optionally substituted aryl, or optionally substituted arylalkyl;
A is hydroxyl, O, S, $NR^{11}$, or optionally substituted nitrogen-containing five-membered heteroaryl or optionally substituted nitrogen-containing bicyclic heteroaryl or bicyclic heterocyclyl,
$R^4$ is hydrogen, hydroxyl, oxo, optionally substituted alkyl, or optionally substituted heteroalkyl,
$R^2$, $R^3$, $R^5$, $R^6$, and $R^7$ are each independently absent, hydrogen, hydroxyl, halogen, optionally substituted a $C_1$-$C_6$ alkyl, optionally substituted a $C_1$-$C_6$ alkoxyl (e.g., methoxyl) or optionally substituted heteroalkyl;
$R^8$ and $R^9$ are each independently selected from a group consisting of hydrogen, a $C_1$-$C_6$ alkyl (e.g., methyl), a halogenated $C_1$-$C_6$ alkyl (e.g., trifluoromethyl) or $C_1$-$C_6$ alkoxyl (e.g., methoxyl), or $R^8$ and $R^9$ form an oxo group;
$R^{10}$ is hydrogen, hydroxyl, optionally substituted alkyl, optionally substituted heteroalkyl, optionally substituted aryl, or optionally substituted arylalkyl where each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;
each heteroalkyl group is an alkyl group in which one or more methyl group is replaced by an independently chosen —O—, —S—, —N($R^{10}$)—, —S(=O)— or —S(=O)$_2$—, where $R^{10}$ is hydrogen, alkyl, or alkyl in which one or more methylene group is replaced by —O—, —S—, —NH, or —N-alkyl;
$R^{11}$ is —$H_2$ or —$HR^{12}$;
$R^{12}$ is $C_1$-$C_6$ alkyl or $C_1$-$C_6$ alkoxy.

The pregnane neurosteroid and pregnenolone neurosteroid of the present invention may each be a compound of Formula IA, wherein X is O;

$R^1$ is hydrogen, —$CH_3$, —$CH_2OH$, 1H-imidazol-1-yl, 1-oxidoquinolin-6-yloxyl and 4-cyano-1H-pyrazol-1'-yl.

$R^4$ is hydrogen, hydroxyl, oxo, optionally substituted alkyl, or optionally substituted heteroalkyl, $R^2$, $R^3$, $R^5$, $R^6$, and $R^7$ are each independently absent, hydrogen, hydroxyl, halogen, optionally substituted a $C_1$-$C_6$ alkyl, optionally substituted a $C_1$-$C_6$alkoxyl (e.g., methoxyl) or optionally substituted heteroalkyl;

$R^8$ and $R^9$ are each independently selected from a group consisting of hydrogen, a $C_1$-$C_6$ alkyl (e.g., methyl), a halogenated $C_1$-$C_6$ alkyl (e.g., trifluoromethyl) or $C_1$-$C_6$alkoxyl (e.g., methoxyl), or $R^8$ and $R^9$ form an oxo group;

$R^{10}$ is hydrogen, hydroxyl, optionally substituted alkyl, optionally substituted heteroalkyl, optionally substituted aryl, or optionally substituted arylalkyl where each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;

each heteroalkyl group is an alkyl group in which one or more methyl group is replaced by an independently chosen —O—, —S—, —N($R^{10}$)—, —S(=O)— or —S(=O)$_2$—, where $R^{10}$ is hydrogen, alkyl, or alkyl in which one or more methylene group is replaced by —O—, —S—, —NH, or —N-alkyl.

The pregnane neurosteroid and pregnenolone neurosteroid of the present invention may each be a compound of Formula IB

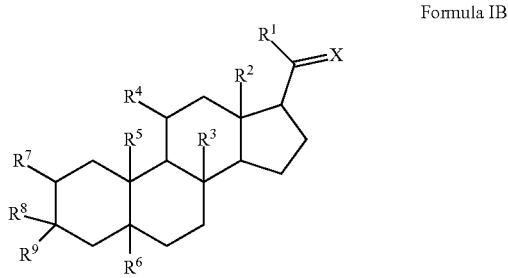

Formula IB or a pharmaceutically acceptable salt thereof, wherein:

X is O, S, or $NR^{10}$;

$R^1$ is hydrogen, hydroxyl, optionally substituted alkyl, optionally substituted heteroalkyl, optionally substituted aryl, or optionally substituted arylalkyl;

$R^4$ is hydrogen, hydroxyl, oxo, optionally substituted alkyl, or optionally substituted heteroalkyl, $R^2$, $R^3$, $R^5$, $R^6$, and $R^7$ are each independently hydrogen, hydroxyl, halogen, optionally substituted alkyl, or optionally substituted heteroalkyl;

$R^8$ is hydrogen or alkyl and $R^9$ is hydroxyl; or $R^8$ and $R^9$ are taken together to form an oxo group;

$R^{10}$ is hydrogen, hydroxyl, optionally substituted alkyl, optionally substituted heteroalkyl, optionally substituted arylalkyl where each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;

each heteroalkyl group is an alkyl group in which one or more methyl group is replaced by an independently chosen —O—, —S—, —N($R^{10}$)—, —S(=O)— or —S(=O)$_2$—, where $R^{10}$ is hydrogen, alkyl, or alkyl in which one or more methylene group is replaced by —O—, —S—, or —N-alkyl.

Compounds of Formula IA and IB include, e.g., allopregnanolone, ganaxolone, alphaxalone, alphadolone, hydroxydione, minaxolone, pregnanolone, acebrochol, or tetrahydrocorticosterone, and pharmaceutically acceptable salts thereof.

The pregnane neurosteroid and pregnenolone neurosteroid of the present invention may also each be a compound of Formula II:

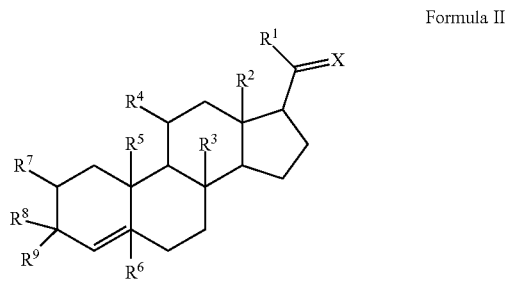

Formula II or a pharmaceutically acceptable salt thereof, wherein:

X is O, S, or $NR^{10}$;

$R^1$ is hydrogen, hydroxyl, —$CH_2A$, optionally substituted alkyl, optionally substituted heteroalkyl, optionally substituted aryl, or optionally substituted arylalkyl;

A is hydroxyl, O, S, $NR^{11}$ or optionally substituted nitrogen-containing bicyclic heteroaryl or bicyclic heterocyclyl, $R^4$ is hydrogen, hydroxyl, oxo, optionally substituted alkyl, or optionally substituted heteroalkyl, $R^2$, $R^3$, $R^5$, $R^6$, and $R^7$ are each independently absent, hydrogen, hydroxyl, halogen, optionally substituted a $C_1$-$C_6$ alkyl, optionally substituted a $C_1$-$C_6$alkoxyl (e.g., methoxyl) or optionally substituted heteroalkyl;

$R^8$ and $R^9$ are each independently selected from a group consisting of hydrogen, a $C_1$-$C_6$ alkyl (e.g., methyl), a halogenated $C_1$-$C_6$ alkyl (e.g., trifluoromethyl) or $C_1$-$C_6$alkoxyl (e.g., methoxyl), or $R^8$ and $R^9$ form an oxo group;

$R^{10}$ is hydrogen, hydroxyl, optionally substituted alkyl, optionally substituted heteroalkyl, optionally substituted aryl, or optionally substituted arylalkyl where each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;

each heteroalkyl group is an alkyl group in which one or more methyl group is replaced by an independently chosen —O—, —S—, —N($R^{10}$)—, —S(=O)— or —S(=O)$_2$—, where $R^{10}$ is hydrogen, alkyl, or alkyl in which one or more methylene group is replaced by —O—, —S—, —NH, or —N-alkyl;

$R^{11}$ is —$H_2$ or —$HR^{12}$;

$R^{12}$ is $C_1$-$C_6$ alkyl or $C_1$-$C_6$ alkoxy.

The pregnane neurosteroid and pregnenolone neurosteroid of the present invention may also each be a compound of Formula III:

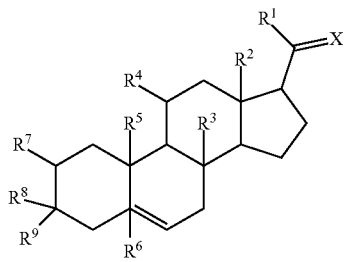

Formula III or a pharmaceutically acceptable salt thereof, wherein:

X is O, S, or $NR^{10}$;

$R^1$ is hydrogen, hydroxyl, $-CH_2A$, optionally substituted alkyl, optionally substituted heteroalkyl, optionally substituted aryl, or optionally substituted arylalkyl;

A is hydroxyl, O, S, $NR^{11}$ or optionally substituted nitrogen-containing bicyclic heteroaryl or bicyclic heterocyclyl, $R^4$ is hydrogen, hydroxyl, oxo, optionally substituted alkyl, or optionally substituted heteroalkyl, $R^2$, $R^3$, $R^5$, $R^6$, and $R^7$ are each independently absent, hydrogen, hydroxyl, halogen, optionally substituted a $C_1$-$C_6$ alkyl, optionally substituted a $C_1$-$C_6$alkoxyl (e.g., methoxyl) or optionally substituted heteroalkyl;

$R^8$ and $R^9$ are each independently selected from a group consisting of hydrogen, a $C_1$-$C_6$ alkyl (e.g., methyl), a halogenated $C_1$-$C_6$ alkyl (e.g., trifluoromethyl) or $C_1$-$C_6$alkoxyl (e.g., methoxyl), or $R^8$ and $R^9$ form an oxo group;

$R^{10}$ is hydrogen, hydroxyl, optionally substituted alkyl, optionally substituted heteroalkyl, optionally substituted aryl, or optionally substituted arylalkyl where each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;

each heteroalkyl group is an alkyl group in which one or more methyl group is replaced by an independently chosen —O—, —S—, —N($R^{10}$)—, —S(═O)— or —S(═O)$_2$—, where $R^{10}$ is hydrogen, alkyl, or alkyl in which one or more methylene group is replaced by —O—, —S—, —NH, or —N-alkyl;

$R^{11}$ is —$H_2$ or —$HR^{12}$;

$R^{12}$ is $C_1$-$C_6$ alkyl or $C_1$-$C_6$ alkoxy.

a) Ganaxolone

Ganaxolone (CAS Reg. No. 38398-32-2,3α-hydroxy-3β-methyl-5α-pregnan-20-one) is the 3β-methylated synthetic analog of allopregnanolone, an endogenous allosteric modulator of CNS GABAA receptors. The structural formula of ganaxolone is:

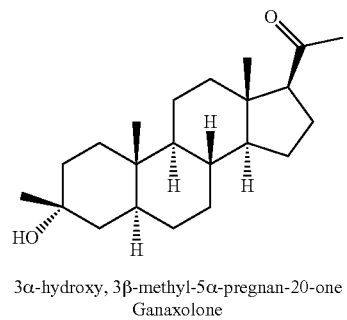

3α-hydroxy, 3β-methyl-5α-pregnan-20-one
Ganaxolone

Ganaxolone has potency and efficacy comparable to allopregnanolone in activating synaptic and extrasynaptic GABAA receptors at a site distinct from benzodiazepines and barbiturates. (Carter 1997) Ganaxolone has protective activity in diverse rodent seizure models (Reddy 2012, Bialer 2010). Clinical studies have demonstrated that ganaxolone has anticonvulsant activity with an acceptable safety and tolerability profile in the dose range of 900 to 1800 mg in adults and children (Sperling 2017, Laxer 2000, Kerrigan 2000, Pieribone 2007). Further, ganaxolone reduces seizures in children with IS and refractory pediatric epilepsy. In an open-label (OL) study, pediatric patients aged 2 to 60 months with refractory seizures and a history of IS were treated with ganaxolone doses up to 36 mg/kg for up to 3 months (Kerrigan 2000). Sixteen of the 20 patients completed treatment, 15 of whom had a history of IS. Five of the 15 patients had a decrease from baseline in the number of spasms of 50%, 5 had a decrease of 25 to 50%, and 5 had a decrease of <25%. One patient became spasm-free and 1 non-responder (with a decrease of <25%) was spasm-free from weeks 2 to 7.

In addition to its anticonvulsant activity, ganaxolone has been shown to reduce anxiety, hyperactivity, and attention in children with fragile X syndrome (Ligsay 2016). Similar behavior problems occur in individuals with TSC, with rates of approximately 50% for ADHD and autism (Jülich & Sahin, 2014). Therefore, ganaxolone treatment may increase GABAA-mediated signaling and improve not only seizure control, but may also ameliorate the behavioral abnormalities in individuals with TSC and TSC-related epilepsy.

Ganaxolone has the same core chemical structure as allopregnanolone, but with the addition of a 3β methyl group designed to prevent conversion back to an entity that is active at nuclear hormone receptors, thereby eliminating the opportunity for unwanted hormonal effects while enhancing the bioavailability of the neurosteroid and preserving its desired CNS activity.

Like allopregnanolone, ganaxolone, (a neuroactive steroid), exhibits potent antiepileptic, anxiolytic, sedative and hypnotic activities in animals by allosterically modulating γ-aminobutyric acid type A (GABAA) receptors in the central nervous system (CNS). Ganaxolone has potency and efficacy comparable to allopregnanolone in activating synaptic and extrasynaptic GABAA receptors at a site distinct from the benzodiazepine site.

Ganaxolone works by interacting with both synaptic and extrasynaptic $GABA_A$ receptors at binding sites which are unique to the class. Outside of the synapse, ganaxolone can be absorbed into the cell membrane and diffuse to activate the extrasynaptic $GABA_A$ receptors, providing constant, or tonal, modulation of the GABA inhibitory signal that calms overexcited neurons.

Ganaxolone is insoluble in water. Its solubilities in 95% alcohol, propylene glycol and polyethylene glycol are 13 mg/mL, 3.5 mg/mL and 3.1 mg/mL, respectively.

Ganaxolone is primarily metabolized by the CYP3A family of liver enzymes, but interactions based on hepatic metabolism are limited to those caused by induction or inhibition of CYP3A4/5 by other drugs such as ketoconazole.

In vitro, the clearance of ganaxolone appears to be driven mainly by CYP3A4. In clinical studies in adults, administration of grapefruit increased the exposure of ganaxolone in healthy volunteers. Levels of ganaxolone were reduced in patients treated concomitantly with enzyme-inducing AEDs. These data further support the hypothesis of CYP3A4 being a major contributor to the clearance of ganaxolone in humans.

In adults, plasma concentrations of ganaxolone after oral administration are characterized by high variability. Single-dose PK parameters were strongly influenced by the rate and extent of ganaxolone absorption, and whether the subjects were in the fed or fasted state.

In the pediatric population, the level of CYP3A4 expression approaches that of adults by approximately 2 years of age (de Wildt et al, 2003), albeit with a high-degree of inter-individual variability. Therefore, patients greater than 2 years of age would be expected to have ganaxolone clearance rates similar to adults.

Ganaxolone has a relatively long half-life—approximately 20 hours in human plasma following oral administration (Nohria, V. and Giller, E., *Neurotherapeutics*, (2007) 4(1): 102-105). Furthermore, ganaxolone has a short $T_{max}$, which means that therapeutic blood levels are reached quickly. Thus initial bolus doses (loading doses) may not be required, which represents an advantage over other treatments. Ganaxolone is useful for treating seizures in adult and pediatric epileptic patients.

Ganaxolone affects GABAA receptors by interacting with a recognition site that is distinct from other allosteric GABAA receptor modulators such as benzodiazepines. Ganaxolone binds to intra- and extrasynaptic receptors, mediating both phasic and tonic modulation, respectively. The unique binding of Ganaxolone to these 2 receptors does not lead to the tolerance seen with benzodiazepines. In contrast to allopregnanolone, ganaxolone is orally bioavailable and cannot be back-converted in the body to intermediates such as progesterone, with classical steroid hormone activity, and as such, does not directly or indirectly via metabolic conversion activate the progesterone receptor.

Ganaxolone administered intravenously was also evaluated and shown to induce burst suppression-like electroencephalogram (EEG) patterns in otherwise normal rats and block seizure response in models that represent clinical status epilepticus (SE). Ganaxolone caused a sedative response but did not cause a full anesthetic response.

In addition to anticonvulsant activity, ganaxolone has been shown to have anxiolytic properties as well as improve behaviours associated with autism. In a mouse model of posttraumatic stress disorder (PTSD), Ganaxolone treatment decreased aggression and social isolation-induced anxiety-like behaviour (Pinna and Rasmussen, 2014). In another study, ganaxolone treatment improved sociability in the BTBR mouse model of autism (Kazdoba et al, 2016). A clinical study of ganaxolone treatment of children and adolescents with fragile X syndrome (FXS), ganaxolone reduced anxiety and hyperactivity and improved attention in those with higher baseline anxiety (Ligsay et al, 2017).

Ganaxalone did not interact with the human ether-a-go-go related gene (hERG) receptor at a measured concentration of 70 nM (n=2). Ganaxolone had no effect on cardiovascular parameters in dogs following a single dose of up to 15 mg/kg (maximum concentration [Cmax] of 1000 ng/mL and area under the concentration time curve (AUC)(0-24) of 10000 n·gh/mL). In the 1-year dog toxicity study (Cmax>1500 ng/mL), transient sinus tachycardia (>190 beats per minute [bpm]) was observed after 3 months of dosing in 4 animals and was accompanied by decreased PR and QT interval but no treatment effect on QRS duration or Q-T interval corrected (QTc). No pulmonary effects were observed in female rats at doses up to 40 mg/kg.

There was a physiologically normal shortening of the PR and QT interval in response to the higher heart rate. There was no effect on QRS duration or QTc interval. No pulmonary effects were observed in female rats at doses up to 40 mg/kg.

Ganaxalone induces major cytochrome P450 (CYP) isoenzymes 1A1/2 and 2B1/2 in female rats but not males. Auto-induction has also been observed in the mouse and rat while no auto-induction has been observed in dogs.

Tissue distribution studies in mice and rats have demonstrated that [$^{14}$C]-ganaxolone was rapidly distributed throughout the body into highly perfused organs, intestine, and adipose tissue, with brain ganaxolone concentrations approximately 5-fold higher than those in plasma.

Most excreted radioactivity in all species is via faeces (>70%) with the remaining excreted in urine.

The most common effect following treatment with ganaxalone in toxicology studies was dose-related sedation, an expected pharmacological effect of a positive modulator of $GABA_A$ receptors. In both the oral and IV programmes, there was little evidence of target organ or systemic toxicity associated with either single- or multiple-dose treatment with ganaxalone. No functional or anatomic changes within haematopoietic tissue or any specific organ such as liver, kidney or gastrointestinal (GI) systems were seen in the repeat-dose studies. In rats, ganaxolone induced hepatic enzymes, with more pronounced effects in females, which were correlated to increased liver weights and dose related hepatocellular hypertrophy in a 6-month study.

In the chronic oral toxicity study in dogs, mean $C_{max}$ levels of greater than 1500 ng/mL (10 and 15 mg/kg/day) were associated with increased weight and total plasma cholesterol levels.

When given IV to rats and dogs, the main dose limiting toxicity finding was sedation. The no observed adverse effect level (NOAEL) after IV dosing in rats for 14 days was established at 42 mg/kg/day for males and 30 mg/kg/day for females. The NOAEL in dog after administration of ganaxolone by IV bolus followed by continuous IV infusion for 28 days was 7.20 mg/kg/day, which corresponded to a steady-state concentration of approximately 330 ng/mL and 333 ng/mL. There were no findings in a local tolerance study in rabbits. Finally, in vitro ganaxalone did not cause haemolysis and was compatible with human plasma.

Ganaxalone was not teratogenic in rats or mice and did not significantly affect the development of offspring. ganaxalone had no effects on fertility and early embryonic development in rats. No potential for mutagenicity was detected. Treatment of neonatal rats with ganaxalone produced expected signs of sedation but did not affect development or demonstrate any post-mortem changes.

b) Allopregnalone

Allopregnanolone (CAS Reg. No. 516-54-1,3α,5α-tetrahydroprogesterone) is an endogenous progesterone derivative with anti-convulsant activity.

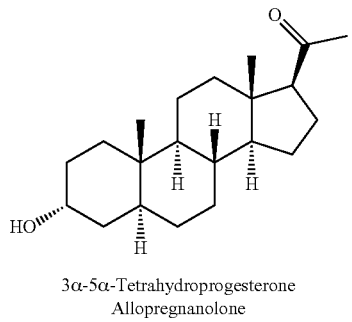

3α-5α-Tetrahydroprogesterone
Allopregnanolone

Allopregnanolone has a relatively short half-life, about 45 minutes in human plasma.

Allopregnanolone exhibits potent antiepileptic, anxiolytic, sedative and hypnotic activities in animals by virtue of its GABAA receptor modulating activity.

In addition to its efficacy in treating seizures, allopregnanolone is being evaluated for use in treating neurodegenerative diseases including Alzheimer's disease, Parkinson's disease, Huntington's disease, and amyotrophic lateral sclerosis and for treating lysosomal storage disorders characterized by abnormalities in cholesterol synthesis, such as Niemann Pick A, B, and C, Gaucher disease, and Tay Sachs disease. (See U.S. Pat. No. 8,604,011, which is hereby incorporated by reference for its teachings regarding the use of allopregnanolone for treating neurological disorders.)

The relationship between progesterone and its metabolite, allopregnanolone, and seizures has been extensively studied in women with catamenial epilepsy, a condition in which there are changes in seizure frequency associated with different phases of the menstrual cycle. At times during the menstrual cycle when progesterone is lower (e.g., perimenopause), the likelihood of seizures tends to increase (French 2005). Circulating allopregnanolone levels parallel those of progesterone. While the reproductive effects of progesterone are related to its interaction with intracellular progesterone receptors, the anticonvulsant effects of progesterone are not (Reddy and Rogawski 2009).

The antiseizure activity of progesterone results from its conversion to the neurosteroid, allopregnanolone (Kokate et al, 1999). Allopregnanolone has been shown to protect against seizure activity in a number of animal models, due to its effects on GABAA receptors (Reddy and Rogawski 2009). Ganaxolone, a synthetic analog of allopregnanolone devoid of progesterone-related effects, may be useful in the treatment of TSC-related epilepsy.

c) Alphaxalone

Alphaxalone, also known as alfaxalone, (CAS Reg. No. 23930-19-0, 3α-hydroxy-5α-pregnan-11,20-dione) is a neurosteroid with an anaesthetic activity. It is used as a general anaesthetic in veterinary practice. Anaesthetics are frequently administered in combination with anti-convulsants for the treatment of refractory seizures. An injectable nanoparticle neurosteroid dosage form containing alphaxalone alone or in combination with either ganaxolone or allopregnanolone is within the scope of this disclosure.

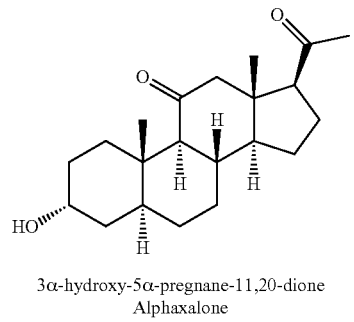

3α-hydroxy-5α-pregnane-11,20-dione
Alphaxalone d) Aphadolone

Alphadolone, also known as alfadolone, (CAS Reg. No. 14107-37-0, 3a, 21-dihydroxy-5α-pregnan-11,20-dione) is a neurosteroid with anaesthetic properties. Its salt, alfadolone acetate is used as a veterinary anaesthetic in combination with alphaxalone.

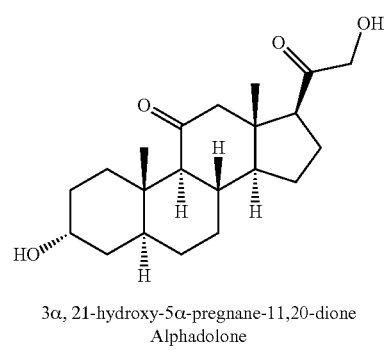

3α, 21-hydroxy-5α-pregnane-11,20-dione
Alphadolone e) Additional Neurosteroids

Additional neurosteroids that may be used in the nanoparticle neurosteroid formulation of this disclosure and the methods disclosed herein include, but are not limited to, pregnenolone, hydroxydione (CAS Reg. No. 303-01-5, (5β)-21-hydroxypregnane-3,20-dione), minaxolone (CAS Reg. No. 62571-87-3, 2β,3α,5α,11α)-11-(dimethylamino)-2-ethoxy-3-hydroxypregnan-20-one), pregnanolone (CAS Reg. No. 128-20-1, (3α,5β)-d-hydroxypreganan-20-one), renanolone (CAS Reg. No. 565-99-1,3α-hydroxy-5(3-pregnan-11,20-dione), or tetrahydrocorticosterone (CAS Reg. No. 68-42-8, 3α,5α-pregnan-20-dione).

Additional neurosteroids that may be used in the nanoparticle neurosteroid formulation of this disclosure and the methods disclosed herein include Co26749/WAY-141839, Co134444, Co177843, and Sage-217, Sage-324 and Sage-718. Co26749/WAY-141839, Co134444, Co177843, and Sage-217 have the following structures:

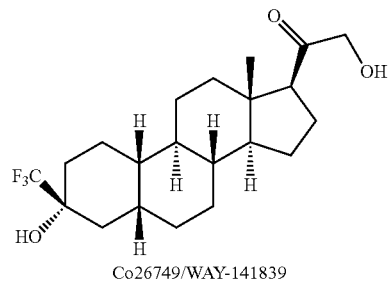

Co26749/WAY-141839

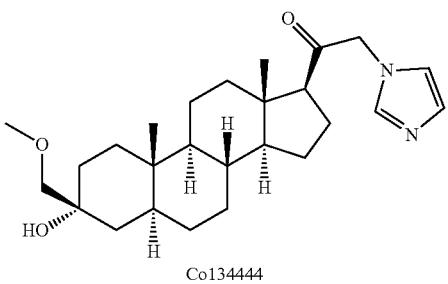
Co134444

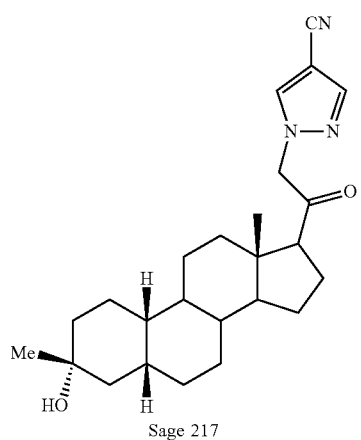
Sage 217

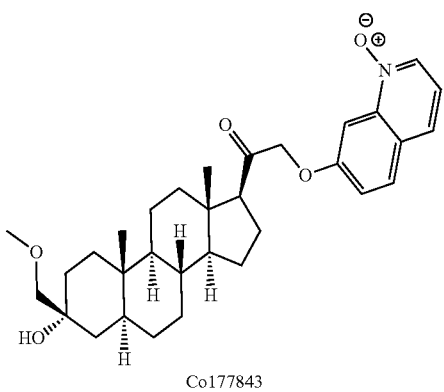
Co177843

Additional neurosteroids that may be used in the nanoparticle neurosteroid formulation of this disclosure and the methods disclosed herein include compounds disclosed in U.S. Patent Publication No. 2016-0229887 (U.S. Ser. No. 14/913,920, filed Feb. 23, 2016), herein incorporated by reference in its entirety.

IV. Dosage

The pregnenolone neurosteroid used in the methods disclosed herein can be administered in the amount of from about 1 mg/day to about 5000 mg/day in one, two, three, or four divided doses. In certain embodiments, doses of 1600 mg/day and 2000 mg/day may be associated with somnolence, and a dose of 1800 mg/day defines the optimal combination of drug exposure, dosing convenience and tolerability.

When the pregnenolone neurosteroid is ganaxolone, a target and maximum dose of ganaxolone is about 1800 mg/day. In these embodiments, this dose provides the highest feasible exposure based on the non-linear kinetics of ganaxolone. Thus, when the pregnenolone neurosteroid is ganaxolone, the amount of ganaxolone administered in the methods disclosed herein is generally from about 200 mg/day to about 1800 mg/day, from about 300 mg/day to about 1800 mg/day, from about 400 mg/day to about 1800 mg/day, from about 450 mg/day to about 1800 mg/day, from about 675 mg/day to about 1800 mg/day, from about 900 mg/day to about 1800 mg/day, from about 1125 mg/day to about 1800 mg/day, from about 1350 mg/day to about 1800 mg/day, from about 1575 mg/day to about 1800 mg/day, or about 1800 mg/day, at a dose of from 1 mg/kg/day to about 80 mg/kg/day in one, two, three or four divided doses. In certain embodiments, the target and maximum dose of ganaxolone may be higher, if necessary, to achieve an improved therapeutic benefit, by be limited by the side effect(s) (e.g., somnolence).

In certain embodiments, from about 300 mg to about 2000 mg, from about 900 mg to about 1800 mg, from about 950 mg to about 1800 mg, from about 1000 mg to about 1800 mg, from about 1100 mg to about 1800 mg, or from about 1200 mg of ganaxolone is orally administered per day, for two or more consecutive days (for example for a time period of from 1 week to 50 years, or for life of the patient. Ganaxolone may be administered orally or parenterally in one, two, three, or four doses, per day.

Whether a human receives ganaxolone twice or three times daily may depend on the formulation. For patients dosing with oral immediate release capsules, ganaxolone is generally administered twice a day, each dose separated from the subsequent and/or previous dose by 8 to 12 hours. For patients taking oral suspension, ganaxolone is generally administered three times a day, each dose separated from the subsequent and/or previous dose by 4 to 8 hours.

When the pregnenolone neurosteroid is ganaxolone, the methods disclosed herein comprise administration of ganaxolone at a dose of from about 1 mg/kg/day to about 80 mg/kg/day, provided that the total amount of administered ganaxolone does not exceed 2000 mg/day.

The methods described herein can further comprise administering ganaxolone at a therapeutically effective amount to achieve a plasma concentration of ganaxolone of 100 ng/ml or higher for approximately 70% or more for a 24 hour-day. In instances, the plasma concentration of ganaxolone may be higher than 100 ng/ml for at least about 70%, about 75%, about 80%, about 85%, about 90%, about 95%, or greater in a 24 hour period.

To achieve a plasma concentration of 100 ng/ml or higher for approximately 70% or more for a 24 hour-day ganaxolone can be administered at least three times a day. Three times a day is preferable, if needed or desired ganaxolone can be administered more than three times a day to achieve the desired trough concentration of ganaxolone. For example, ganaxolone may be administered three times a day, four times a day, five times a day, six times a day, seven times a day, eight times a day or more.

Ganaxolone administered in accordance with the methods disclosed herein can be administered at the same or a lower daily dose that have been used in clinical trials, and can increase drug exposure by maintaining a ganaxolone serum concentration of at least about 100 ng/ml, e.g. for at least about 70% or more of a 24 hour day. A total daily dose of about 1800 mg, about 1700 mg, about 1600 mg, about 1500 mg or 63 mg/kg/day of ganaxolone can be administered, provided that the total daily dose is administered in three or more separate administrations (which preferably each contain the same amount of ganaxolone) to produce a ganaxolone concentration of at least about 100 ng/ml for at least 70% or more for a 24-hour day. Typically, a total daily dose of 1500 mg per day of ganaxolone can produce a plasma concentration of at least about 100 ng/ml or greater for approximately 70% or more over a 24 hour-day when administered three times a day during the day.

For example, when a total daily dose of 1500 mg of ganaxolone is administered, a dose of about 500 mg three times a day can be administered. For example, when a total daily dose of 1800 mg of ganaxolone is administered, a dose of 600 mg three times a day can be administered. The maximum daily dose of ganaxolone is administered at the same or varying doses across at least three intervals in a 24 hour period. A skilled clinician will understand that the amount of ganaxolone administered at least three times a day can be adjusted to achieve the desired ganaxolone trough level so long as the total amount does not exceed the maximum daily dose of ganaxolone.

While a plasma concentration of at least about 100 ng/ml is preferable, there can be some variability based on, for example, differences in subjects' weight, metabolism, age, duration of seizure and severity of seizure.

Ganaxolone can be administered orally (e.g., as an oral suspension or an oral capsule) or an intravenous formulation. Preferably, ganaxolone is administered orally. Oral administration can include, but not limited to, oral suspension formulations and oral capsules.

A plasma concentration of at least about 100 ng/ml or higher for approximately 70% or more of a 24 hour-day results in improved seizure reduction and/or suppression of seizure. For example, a seizure reduction of at least 20% or greater relative to baseline seizure frequency can be achieved. For example, a seizure reduction of at least 35% or greater relative to baseline frequency can be achieved. Seizure burden and/or frequency can be monitored using EEG.

The pharmacokinetics of ganaxolone in formulations comprising immediate release 0.3-micron particles (e.g., the formulation of Example 2) are linear through approximately 1200 mg/day (given twice-a-day ("BID")), with a modest increase in exposure at a dose of 1600 mg/day, and little or no further increase in exposure at a dose of 2000 mg/day. Therefore, to maintain as high a trough level as possible in all subjects, a dose of 1800 mg/day is generally targeted, but maybe adjusted higher or lower in certain individuals to provide for optimal therapeutic effect.

In certain embodiments, ganaxolone is administered at a dose of more than 5 mg/kg/day, for example a dose of from about 6 mg/kg/day to about 80 mg/kg/day, provided that the total amount of administered ganaxolone does not exceed 1800 mg/day.

In certain embodiments, the dose of ganaxolone is adjusted in 15 mg/kg/day up to 100 mg/kg/day up to the maximum dose of 1800 mg per day during treatment.

In certain embodiments, the method of treatment comprises administering at least 33 mg/kg/day of ganaxolone in one, two, three, or four doses, with a maximum daily dose of about 1800 mg.

In certain embodiments, the human is from about of 0.6 and about 7 years old and is administered a dose of ganaxolone of from about 1.5 mg/kg (twice-a-day ("BID") (3 mg/kg/day) to 12 mg/kg (three times a day ("TID") (36 mg/kg/day). In the embodiments, where the human receives 12 mg/kg TID dose regimen, and the trough concentrations of at least about 38.5±37.4 ng/mL is achieved.

In certain embodiments, ganaxolone is administered orally at doses of 6 mg/kg BID (12 mg/kg/day) to 12 mg/kg TID (36 mg/kg/day) in a O-cyclodextrin formulation with food, and ganaxolone's plasma concentrations of up to 22.1 ng/mL and 5.7 to 43.7 ng/mL are achieved at week 4 and week 8, respectively, of the administration.

In certain embodiments, ganaxolone is administered orally with food at doses of 1 to 12 mg/kg TID (3 to 36 mg/kg/day), and ganaxolone plasma concentrations of up to 5.78 ng/mL (1 mg/kg TID) to 10.3 to 16.1 ng/mL (12 mg/kg TID) are achieved.

In certain embodiments, ganaxolone orally at a dose of 3 to 18 mg/kg TID (9 to 54 mg/kg/day) in an oral suspension formulation, and ganaxolone $C_{max}$ of about 123 ng/mL and a trough concentration of about 23 ng/mL is achieved.

In certain embodiments, mean ganaxolone $C_{min}$ (trough) are from 55 ng/ml to about 100 ng/ml, and $C_{max}$ levels are from about 240 ng/ml to 400 ng/ml (e.g., 262 ng/mL), based on three-times-a-day oral administration of 1000 mg ganaxolone.

In certain embodiments, the methods result in mean $C_{min}$ (trough) and $C_{max}$ levels are about 56.9 ng/ml and about 262 ng/mL, respectively, based on twice-a-day oral administration of 1000 mg ganaxolone.

In certain embodiments, administration of ganaxolone provides a $C_{min}/C_{max}$ ratio of greater than 3, 3.5, 4, 4.5, 5, or 6. This $C_{min}/C_{max}$ ratio may be provided after a single dose administration and/or after administration at steady-state. In certain embodiments, the $C_{min}/C_{max}$ ratio remains the same, regardless of the dose of ganaxolone administered.

In certain embodiments, the dose administered is determined from a pediatric pharmacokinetic model that allows a determination of the dose of ganaxolone in the various pediatric age ranges that will produce a $C_{max}$ and AUC exposure similar to that achieved following an efficacious dose determined in the adult epilepsy population. The model could, e.g., be constructed with standard methods with consideration of the pharmacokinetic data in the present application.

In certain embodiments, the pregnenolone neurosteroid may be administered to the patient using a number of titration steps until a therapeutically effective dosage regimen is attained. For example, about six-eight titration steps may be used, depending on the size of the patient.

In certain embodiments, the methods disclosed herein comprises establishing a baseline seizure frequency for the patient, initially administering a dose of ganaxolone to the patient in an amount from about 0.5 mg/kg/day to about 15 mg/kg/day; and progressively increasing the dose of ganaxolone over the course of 4 weeks to an amount from about 18 mg/kg/day to about 60 mg/kg/day, wherein the total dose of ganaxolone is up to about 1800 mg/day for patients whose body weight is greater than 30 kg. For patients whose body weight is 30 kg or less, the total dose of ganaxolone per day may be less (e.g., about 63 mg/day). In certain preferred embodiments, the initial dose of ganaxolone is about 4.5 mg/kg/day. In certain preferred embodiments, the ganaxolone dose is increased to about 36 mg/kg/day. In certain preferred embodiments, the ganaxolone dose is decreased to a prior level if the patient experiences dose-limiting adverse events.

In certain embodiments, for subjects weighing more than 30 kg, treatment is initiated at a dose of 900 mg/day in divided doses. The dose is then increased by approximately 20 to 50% (e.g., an increase from 900 mg/day to 1200 mg/day is a 33% increase) at intervals of not less than 3 days and not more than 2 weeks, provided that the current dose is reasonably tolerated, until desired efficacy is achieved or a maximally tolerated dose (MTD) level is reached. Subsequent dose adjustments may be made in increments of approximately 20 to 50% with a minimum of 3 days between dose changes, unless required for safety. The maximum allowable dose in these embodiments is 1800 mg/day.

In certain embodiments, for subjects weighing 30 kg, or less, treatment is initiated at 18 mg/kg/day and may be increased in about 20% to 50% increments at intervals of not less than 3 days and not more than 2 weeks, provided that the current dose is reasonably tolerated, until desired efficacy is achieved or a maximally tolerated dose (MTD) level is reached. Subsequent dose adjustments may be made in increments of approximately 20% to 50% with a minimum of 3 days between dose changes, unless required for safety. The maximum allowable dose these embodiments is 63 mg/kg/day.

For humans weighing ≥28 kg (62 lbs), ganaxolone may be initiated at a dose of from about 300 mg/day to about 600 mg/day (e.g., 400 mg/day) in divided doses. The dose will be increased 450 mg/day every 7 days until 1800 mg/day is reached or a maximum tolerated dose.

For humans weighing <28 kg (62 lbs), ganaxolone may be initiated at a dose of from about 10 mg/kg/day to about 30 mg/kg/day (e.g., 18 mg/kg/day), increasing approximately 15 mg/kg/day every week until 63 mg/kg/day is reached.

In certain embodiments, ganaxolone is administered in increments of from 10 mg/day to 20 mg/day (e.g., 15 mg/kg/day) up to 63 mg/kg/day (maximum 1800 mg/day) as an oral suspension or in increments of from 225 mg/day to 900 mg/day (e.g., 450 mg/day) as an oral capsule. In some of these embodiments, ganaxolone may, e.g., be dosed as follows: 6 mg/kg three times daily (TID) (18 mg/kg/day) suspension/225 twice daily (BID) (450 mg/day) capsules—Days 1-7; 11 mg/kg TID (33 mg/kg/day) suspension/450 BID (900 mg/day) capsules—Days 8-14; 16 mg/kg TID (48 mg/kg/day) suspension/675 BID (1350 mg/day) capsules—Days 15-21; 21 mg/kg TID (63 mg/kg/day not to exceed 1800 mg/day) suspension/900 BID (1800 mg/day) capsules—Days 22-28.

In certain embodiments, ganaxolone is administered in oral suspension, and the following titration schedule is used:

| 15 kg (33 lbs) | | | | | |
|---|---|---|---|---|---|
| Titration Step# | mg/kg | Dose (mg) | Dose mg/kg increase | Total mg change | % Dose Change | Total ml Suspension |
| 1 | 18 | 270 | | | | 5.4 |
| 2 | 24 | 359 | 6 | 89 | 33% | 7.2 |
| 3 | 32 | 478 | 8 | 119 | 33% | 9.6 |
| 4 | 42 | 635 | 11 | 158 | 31% | 12.7 |
| 5 | 54 | 810 | 12 | 175 | 27% | 16.2 |
| 6 | 63 | 945 | 9 | 135 | 16% | 18.9 |

| 20 kg (44 lbs) | | | | | | |
|---|---|---|---|---|---|---|
| Titration Step# | mg/kg | Dose (mg) | Dose change (mg/kg) | Total mg change | % Dose Change | Total ml Suspension |
| 1 | 18 | 360 | | | | 7.2 |
| 2 | 24 | 479 | 6 | 119 | 33% | 9.6 |
| 3 | 32 | 637 | 8 | 158 | 33% | 12.7 |
| 4 | 42 | 847 | 10 | 210 | 31% | 16.9 |
| 5 | 54 | 1083 | 12 | 233 | 27% | 21.6 |
| 6 | 63 | 1260 | 9 | 180 | 16% | 25.2 |

| 25 kg (55 lbs) | | | | | | |
|---|---|---|---|---|---|---|
| Titration Step# | mg/kg | Dose (mg) | 005* change (mg/kg) | Total mg change | % Dose Change | Total ml Suspension |
| 1 | 18 | 450 | | | | 9.0 |
| 2 | 24 | 599 | 6 | 149 | 33% | 12.0 |
| 3 | 32 | 796 | 8 | 198 | 33% | 15.9 |
| 4 | 42 | 1059 | 10 | 263 | 31% | 21.2 |
| 5 | 54 | 1350 | 12 | 291 | 27% | 27.0 |
| 6 | 63 | 1575 | 9 | 225 | 16% | 31.5 |

| 30 kg (66 lbs) | | | | | | |
|---|---|---|---|---|---|---|
| Titration Step# | mg/kg | Dose (mg) | Dose change (mg/kg) | Total mg change | % Dose Change | Total ml Suspension |
| 1 | 18 | 540 | | | | 10.8 |
| 2 | 24 | 718 | 6 | 178 | 33% | 14.4 |
| 3 | 32 | 955 | 8 | 237 | 33% | 19.1 |
| 4 | 42 | 1270 | 10 | 315 | 31% | 25.4 |
| 5 | 50 | 1500 | 8 | 230 | 18% | 30.0 |
| 6 | 55 | 1650 | 5 | 150 | 11% | 33.0 |
| 7 | 60 | 1800 | 5 | 150 | 9% | 36.0 |

In certain embodiments, ganaxolone is administered in capsules and the following titration schedule is used:

| | 200 mg capsules | | | 225 mg capsules | | |
|---|---|---|---|---|---|---|
| Titration Step | Total Daily Dose | No. Caps AM | No. Caps PM | Total Daily Dose | No. Caps AM | No. Caps PM |
| 1 | 400 | 1 | 1 | 450 | 1 | 1 |
| 2 | 600 | 1 | 2 | 675 | 1 | 2 |
| 3 | 800 | 2 | 2 | 900 | 2 | 2 |
| 4 | 1000 | 2 | 3 | 1125 | 2 | 3 |
| 5 | 1200 | 3 | 3 | 1350 | 3 | 3 |
| 6 | 1400 | 3 | 4 | 1575 | 3 | 4 |
| 7 | 1600 | 4 | 4 | 1800 | 4 | 4 |
| 8 | 1800 | 4 | 5 | | | |

In certain embodiments, the trough concentrations associated with maximal efficacy are in the range of about 55 ng/mL, about 60 ng/ml or about 65 ng/ml (0.3 micron suspension; TID dosing) and a dose of 1800 mg/day (0.3 micron capsules, BID dosing) provides trough plasma concentrations in this range.

Methods of treatment disclosed herein encompass administration of neurosteroid (e.g., ganaxolone) with or without food. In certain embodiments, ganaxolone is administered with food.

V. Treatment Duration

Treatment duration in accordance with the methods disclosed herein may range from 1 day to more than 2 years. For example, treatment duration may be from about 1 day to about 80 years, from about 1 day to about 70 years, from about 1 day to about 60 years, from about 1 day to about 50 years, from about 1 day to about 45 years, from about 2 days to about 45 years, from about 2 days to about 40 years, from about 5 days to about 35 years, from about 10 days to 30 about years, from about 10 day to about 30 years, from about 15 days to about 30 years. In some embodiments, the treatment duration is for as long as the subject continues to derive a therapeutic benefit from administration of the neurosteroid (e.g., ganaxolone). In some embodiments, the treatment duration is 14 days, 28 days, 30 days, 6 weeks, 8 weeks, 10 weeks, 12 weeks, 6 months, 1 year, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, or 10 years.

In certain embodiments, at the conclusion of the treatment period, or upon discontinuation of the treatment, the dose is gradually decreased over a period of 1 to 4 weeks, based on subject's age, weight, dose and duration of the treatment.

VI. Formulations

Any desired formulation that comprises a pregnenolone neurosteroid (e.g., ganaxolone) and one or more pharmaceutically acceptable excipient(s) can be administered according to the methods disclosed herein. The pregnenolone neurosteroid is included in a therapeutically effective amount to treat one more symptom(s) of TSC or TSC-related epilepsy. In certain embodiments, the formulations are free from cyclodextrins, including sulfoalkyl ether cyclodextrins and modified forms thereof.

In the preferred embodiments, the amount of the pregnenolone neurosteroid in the formulation is therapeutically effective to treat a symptom of TSC-related epilepsy, for example, after oral administration of the formulation for 1 week and/or 2 weeks and/or 3 weeks and/or 4 weeks and/or 6 weeks and/or 7 weeks, and/or 8 weeks, and/or 9 weeks and/or 10 weeks and/or 11 weeks and/or 12 weeks, or longer.

In preferred embodiments, the pregnenolone neurosteroids (e.g. ganaxolone) are incorporated into a pharmaceutically acceptable composition for oral administration. Such a formulation in certain preferred embodiments may be a liquid (e.g., an aqueous liquid (encompassing suspensions, solutions and the like). In other preferred embodiments, the oral formulation may be an oral solid dosage form (e.g., an oral capsule or tablet). In most preferred embodiments, the oral formulation is an oral suspension comprising the pregnenolone neurosteroid or an oral capsule comprising the pregnenolone neurosteroid. Preferably, a unit dose of the oral formulation contains a therapeutically effective amount of the pregnenolone neurosteroid which can be orally administered to the (e.g., human) patient (e.g., an infant, child, adolescent or adult). In certain embodiments, the oral suspension is administered to the patient via the use of an oral syringe. For example, it is contemplated that the oral suspension is utilized for humans who weigh less than about 30 kg (e.g., about 28 kg). On the other hand, the oral suspension may be administered humans who would have trouble swallowing a solid oral dosage form. Children larger than 30 kg may take a solid dosage form, e.g., ganaxolone capsules. The ganaxolone oral suspension may be administered through an oral dosing syringe, e.g., three times daily. The ganaxolone capsules may be administered, e.g., twice daily. The patients experience better absorption of the ganaxolone with meals (milk).

As described in U.S. Pat. No. 8,022,054, the liquid formulation may be an aqueous dispersion of stabilized pregnenolone neurosteroid (e.g., ganaxolone) particles comprising ganaxolone, a hydrophilic polymer, a wetting agent, and an effective amount of a complexing agent that stabilizes particle growth after an initial particle growth and endpoint is reached, the complexing agent selected from the group of small organic molecules having a molecular weight less than 550 and containing a moiety selected from the group consisting of a phenol moiety, an aromatic ester moiety and an aromatic acid moiety, wherein the stabilized particles have a volume weighted median diameter (D50) of the particles from about 50 nm to about 500 nm, the complexing agent being present in an amount from about 0.05% to about 5%, w/w based on the weight of particles, the particles dispersed in an aqueous solution which further contains at least two preservatives in an amount sufficient to inhibit microbial growth. The hydrophilic polymer may be in an amount from about 3% to about 50%, w/w, based on the weight of the solid particles. The wetting agent may be an amount from about 0.01% to about 10%, w/w, based on the weight of the solid particles. The pregnenolone neurosteroid (e.g., ganaxolone) may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. The aqueous dispersion may further comprise a sweetener, e.g., sucralose. The preservative is selected from the group consisting of potassium sorbate, methylparaben, propylparaben, benzoic acid, butylparaben, ethyl alcohol, benzyl alcohol, phenol, benzalkonium chloride, and mixtures of any of the foregoing.

In some embodiments, liquid pregnenolone neurosteroid (e.g., ganaxolone) formulations are provided comprising the ganaxolone particles described herein and at least one dispersing agent or suspending agent for oral administration to a subject. The ganaxolone formulation may be a powder and/or granules for suspension, and upon admixture with water, a substantially uniform suspension is obtained. As described herein, the aqueous dispersion can comprise amorphous and non-amorphous ganaxolone particles of consisting of multiple effective particle sizes such that ganaxolone particles having a smaller effective particle size are absorbed more quickly and ganaxolone particles having a larger effective particle size are absorbed more slowly. In certain embodiments the aqueous dispersion or suspension is an immediate release formulation. In another embodiment, an aqueous dispersion comprising amorphous ganaxolone particles is formulated such that about 50% of the ganaxolone particles are absorbed within about 3 hours after administration and about 90% of the ganaxolone particles are absorbed within about 10 hours after administration. In other embodiments, addition of a complexing agent to the aqueous dispersion results in a larger span of ganaxolone containing particles to extend the drug absorption phase such that 50-80% of the particles are absorbed in the first 3 hours and about 90% are absorbed by about 10 hours.

A suspension is "substantially uniform" when it is mostly homogenous, that is, when the suspension is composed of approximately the same concentration of pregnenolone neurosteroid (e.g., ganaxolone) at any point throughout the suspension. Preferred embodiments are those that provide concentrations essentially the same (within 15%) when measured at various points in a ganaxolone aqueous oral formulation after shaking. Especially preferred are aqueous suspensions and dispersions, which maintain homogeneity (up to 15% variation) when measured 2 hours after shaking. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, the pregnenolone neurosteroid (e.g., ganaxolone) powders for aqueous dispersion described herein comprise stable ganaxolone particles having an effective particle size by weight of less than 500 nm formulated with ganaxolone particles having an effective particle size by weight of greater than 500 nm. In such embodiments, the formulations have a particle size distribution wherein about 10% to about 100% of the ganaxolone particles by weight are between about 75 nm and about 500 nm, about 0% to about 90% of the ganaxolone particles by weight are between about 150 nm and about 400 nm, and about 0% to about 30% of the ganaxolone particles by weight are greater than about 600 nm. The ganaxolone particles describe herein can be amorphous, semi-amorphous, crystalline, semi-crystalline, or mixture thereof.

In one embodiment, the aqueous suspensions or dispersions described herein comprise ganaxolone particles or ganaxolone complex at a concentration of about 20 mg/ml to about 150 mg/ml of suspension. In another embodiment, the aqueous oral dispersions described herein comprise ganaxolone particles or ganaxolone complex particles at a concentration of about 25 mg/ml to about 75 mg/ml of solution. In yet another embodiment, the aqueous oral dispersions described herein comprise ganaxolone particles or ganaxolone complex at a concentration of about 50 mg/ml of suspension. The aqueous dispersions described herein are especially beneficial for the administration of ganaxolone to infants (less than 2 years old), children under 10 years of age and any patient group that is unable to swallow or ingest solid oral dosage forms.

Liquid pregnenolone neurosteroid (e.g., ganaxolone) formulation dosage forms for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, 2.sup.nd Ed., pp. 754-757 (2002). In addition to ganaxolone particles, the liquid dosage forms may comprise additives, such as: (a) disintegrating agents; (b) dispersing agents; (c) wetting agents; (d) at least one preservative, (e) viscosity enhancing agents, (f) at least one sweetening agent, (g) at least one flavoring agent, (h) a complexing agent. and (i) an ionic dispersion modulator. In some embodiments, the aqueous dispersions can further comprise a crystalline inhibitor.

Examples of disintegrating agents for use in the aqueous suspensions and dispersions include, but are not limited to, a starch, e.g., a natural starch such as corn starch or potato starch, a pregelatinized starch such as National 1551 or Amijele®, or sodium starch glycolate such as Promogel® or Explotab®; a cellulose such as a wood product, microcrystalline cellulose, e.g., Avicel®, Avicel® PH101, Avicel® PH102, Avicel® PH105 Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethylcellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908%).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and 0.005% to 0.03% propylparaben by weight to the total aqueous dispersion weight. In yet another embodiment, the aqueous liquid dispersion can comprise methylparaben 0.05 to about 0.1 weight % and propylparaben from 0.01-0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet®. Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid pregnenolone neurosteroid (e.g., ganaxolone) formulations can also comprise inert diluents commonly used in the art, such as water or other solvents, solubilizing agents, and emulsifiers.

In some embodiments, the pharmaceutical pregeneolone neurosteroid (e.g., ganaxolone) formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960,563, each of which is specifically incorporated by reference.

Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In certain preferred embodiments, the liquid pharmaceutical formulation comprises ganaxolone, hydroxypropyl methylcellulose, polyvinyl alcohol, sodium lauryl sulfate, simethicone, methyl paraben, propyl paraben, sodium benzoate, citric acid, and sodium citrate at pH 3.8-4.2. The suspension may comprise ganaxolone at a concentration of 50 mg/ml. The formulation may further comprise a pharmaceutically acceptable sweetener (e.g., sucralose) and/or a pharmaceutically acceptable flavorant (e.g., cherry). The formulation may be enclosed, e.g., in a 120 mL, 180 mL, 240 mL, or 480 mL bottle.

In certain preferred embodiments, an oral solid formulation as described and prepared in Applicant's prior U.S. Pat. No. 7,858,609, entitled "Solid Ganaxolone Formulations and Methods for the Making and Use Thereof", hereby incorporated by reference in its entirety is used. The oral solid dosage formulation of pregnenolone neurosteroid (e.g., oral capsule or tablets) may be prepared in accordance with any suitable methods For example, as disclosed in U.S. Pat. No. 7,858,609, the oral solid formulation comprises stabilized particles comprising the pregenolone neurosteroid (e.g., ganaxolone), a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm, the complexing agent being present in an amount from about 0.05% to about 5% w/w, based on the weight particles of the solid. The hydrophilic polymer may be in an amount from about 3% to about 50%, w/w, based on the weight of the solid particles. The wetting agent may be an amount from about 0.01% to about 10%, w/w, based on the weight of the solid particles. The pregnenolone neurosteroid (e.g., ganaxolone) may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. The solid stabilized particles may be combined with optional excipients and prepared for administration in the form of a powder, or they may be incorporated into a dosage form selected from the group consisting of a tablet or capsule. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. When the particles are incorporated into a solid dosage form, the solid dosage form may further comprise at least one pharmaceutically acceptable excipient, e.g., an ionic dispersion modulator, a water soluble spacer, a disintegrant, a binder, a surfactant, a plasticizer, a lubricant, a diluent and any combinations or mixtures thereof. The water soluble spacer may be a saccharide or an ammonium salt, e.g., fructose, sucrose, glucose, lactose, mannitol. The surfactant may be, e.g., polysorbate. The plasticizer may be, e.g., polyethylene glycol. The disintegrant may be cross-linked sodium carboxymethylcellulose, crospovidone, mixtures thereof, and the like.

A capsule may be prepared, e.g., by placing the bulk blend pregnenolone neurosteroid (e.g., ganaxolone) formulation, described above, inside of a capsule. In some embodiments, the ganaxolone formulations (non-aqueous suspensions and solutions) are placed in a soft gelatin capsule. In other embodiments, the ganaxolone formulations are placed in standard gelatin capsules or non-gelatin capsules such as capsules comprising HPMC. In other embodiments, the ganaxolone formulations are placed in a sprinkle capsule, wherein the capsule may be swallowed whole or the capsule may be opened and the contents sprinkled on food prior to eating. The therapeutic dose can be split into multiple (e.g., two, three, or four) capsules. In some embodiments, the entire dose of the ganaxolone formulation is delivered in a capsule form.

Preferably, each capsule contains about 200 to about 600 mg ganaxolone, about 300 to about 600 mg ganaxolone, about 400 to about 600 mg ganaxolone, about 500 to about 600 mg ganaxolone, about 200 mg ganaxolone, about 250 mg ganaxolone, about 300 mg ganaxolone, about 500 mg ganaxolone or about 600 mg ganaxolone.

In certain embodiments, each capsule contains either 200 mg or 225 mg ganaxolone, and hydroxypropyl methylcellulose, sucrose, polyethylene glycol 3350, polyethylene glycol 400, sodium lauryl sulfate, sodium benzoate, citric acid anhydrous, sodium methyl paraben, microcrystalline cellulose, 30% Simethicone Emulsion, gelatin capsules, polysorbate 80, and sodium chloride. In some of the embodiments, the size of the capsule is 00.

Alternatively, the oral dosage forms may be in the form of a controlled release dosage form, as described in U.S. Pat. No. 7,858,609.

The pregnenolone neurosteroid (e.g., ganaxolone) formulations suitable may also be administered parenterally. In such embodiments, the formulations are suitable for intramuscular, subcutaneous, or intravenous injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethyleneglycol, glycerol, cremophor and the like), suitable mixtures thereof, vegetable oils (such as olive oil) and injectable organic esters such as ethyl oleate. Additionally, Ganaxolone can be dissolved at concentrations of >1 mg/ml using water soluble beta cyclodextrins (e.g. beta-sulfobutyl-cyclodextrin and 2-hydroxypropylbetacyclodextrin). A particularly suitable cyclodextrin is a substituted-β-cyclodextrin is Captisol®. Proper fluidity can be maintained, for example, by the use of a coating such as lecithin, by the maintenance of the required particle size in the case of dispersions, and by the use of surfactants. Ganaxolone formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. Ganaxolone suspension formulations designed for extended release via subcutaneous or intramuscular injection can avoid first pass metabolism and lower dosages of ganaxolone will be necessary to maintain plasma levels of about 50 ng/ml. In such formulations, the particle size of the ganaxolone particles and the range of the particle sizes of the ganaxolone particles can be used to control the release of the drug by controlling the rate of dissolution in fat or muscle.

Particularly useful injectable formulations are disclosed in Applicant's U.S. Patent Publication No. 2017/0258812 (U.S. Ser. No. 15/294,135, filed Oct. 14, 2016), herein incorporated by reference in its entirety. Other useful injectable formulations of pregnenolone neurosteroids known to those skilled in the art can also be used.

VII. Combination Treatment

The disclosure includes embodiments in which the neurosteroid is the only active agent and embodiments in which the neurosteroid is administered in combination with one or more additional active agents. When used in combination with an additional active agent the neurosteroid and the additional active agent may be combined in the same formulation or may be administered separately. The neurosteroid may be administered while the additional active agent is being administered (concurrent administration) or may be administered before or after the additional active agent is administered (sequential administration).

The disclosure includes embodiments in which the additional active agent is an anti-convulsant. Anticonvulsants include GABAA receptor modulators, sodium channel blocker, GAT-1 GABA transporter modulators, GABA transaminase modulators, voltage-gated calcium channel blockers, and peroxisome proliferator-activated alpha modulators.

The disclosure includes embodiments in which the patient is given an anesthetic or sedative in combination with a neurosteroid. The anesthetic or sedative may be administered at a concentration sufficient to cause the patient to lose consciousness, such as a concentration sufficient to medically induce coma or a concentration effective to induce general anesthesia. Or the anesthetic or sedative may be given at a lower dose effective for sedation, but not sufficient to induce a loss of consciousness.

Benzodiazepines are used both as anticonvulsants and anesthetics. Benzodiazepines useful as anaesthetics include diazepam, flunitrazepam, lorazepam, and midazolam.

In certain embodiments, neurosteroid is administered concominatly with a benzodiazepine (e.g., clobazam, diazepam, clonazepam, midazolam, clorazepic acid, Levetiracetam, felbamate, lamotrigine, a fatty acid derivative (e.g., valproic acid), a carboxamide derivative (rufinamide, carbamazepine, oxcarbazepine, etc.), an amino acid derivative (e.g., levocarnitine), a barbiturate (e.g., phenobarbital), or a combination of two or more of the foregoing agents.

The neurosteroid nanoparticle injectable formulation of this disclosure may be administered with another anticonvulsant agent. Anticonvulsants include a number of drug classes and overlap to a certain extent with the coma-inducing, anesthetic, and sedative drugs that may be used in combination with a neurosteroid. Anticonvulsants that may be used in combination with the neurosteroid nanoparticle injectable formulation of this disclosure include aldehydes, such as paraldehyde; aromatic allylic alcohols, such as stiripentol; barbiturates, including those listed above, as well as methylphenobarbital and barbexaclone; benzodiazepines include alprazolam, bretazenil, bromazepam, brotizolam, chloridazepoxide, cinolazepam, clonazepam, chorazepate, clopazam, clotiazepam, cloxazolam, delorazepam, diazepam, estazolam, etizolam, ethyl loflazepate, flunitrazepam, flurazepam, flutoprazepam, halazepam, ketazolam, loprazolam, lorazepam, lormetazepam, medazepam, midazolam, nimetazepam, nitrazepam, nordazepam, oxazepam, phenenazepam, pinazepam, prazepam, premazepam, pyrazolam, quazepam, temazepam, tatrazepam, and triazolam; bromides, such as potassium bromide; carboxamides, such carbamazepine, oxcarbazepine, and eslicarbazepine acetate; fatty acids, such as valproic acid, sodium valproate and divalproex sodium; fructose derivatives, such as topiramate; GABA analogs such as gabapentin and pregabalin, hydantoins, such as ethotoin, phenytoin, mephenytoin, and fosphenytoin; other neurosteroids, such as allopregnanolone, oxasolidinediones, such as paramethadione, trimethadione, and ethadione, propionates such as beclamide; pyrimidinediones such as primidone, pyrrolidines such as brivaracetam, levetiracetam, and seletracetam, succinimides, such as ethosuximide, pensuximide, and mesuximide; sulfonamides such as acetazoloamide, sultiame, methazolamide, and zonisamide; triazines such as lamotrigine, ureas such as pheneturide and phenacemide; NMDA antagonists, such as felbamate, and valproylamides such as valpromide and valnoctamide; and perampanel.

VIII. Biomarker

Predictive biomarkers are used to identify patient populations that are more homogenous and have a higher propensity to respond to a therapy.

Allopregnanolone, a metabolite of progesterone, is a positive allosteric modulator (PAM) of the GABAA-receptor. Humans suffering from TSC-related epilepsy may exhibit this allopregnanolone deficiency supporting the hypothesis that treatment with a pharmaceutically acceptable pregnenolone (e.g., ganaxolone) may reduce seizure frequency and, possibly, improve additional symptoms of TSC-related epilepsy.

Thus, in certain embodiments, allopregnanolone-sulfate (Allo-S) is used as a predictive biomarker for a response to ganaxolone, an analog of allopregnanolone. In these embodiments, Allo-S plasma level of 2,500 pg mL$^{-1}$ or less indicates that a subject is likely to respond and benefit from ganaxolone therapy; and a plasma level of Allo-S plasma level of above 2,500 pg mL$^{-1}$ indicates that a subject is unlikely to respond to ganaxolone therapy and that a different therapeutic agent should be used.

5. EXAMPLES

The following examples of formulations in accordance with the present invention are not to be construed as limiting the present invention in any manner and are only samples of the various formulations described herein.

During the development of ganaxolone formulations, a variety of formulations have been evaluated to establish a formulation that demonstrates adequate pharmacokinetic ("PK") parameters and is suitable for development and commercialisation. Other formulations of ganaxolone used included ganaxolone mixed with sodium lauryl sulfate, with hydroxypropyl-beta-cyclodextrin (HP-β-CD) in solution, and with beta cyclodextrin (β-CD) administered as a variety of suspensions, as well as ganaxolone 0.5 micron particles in suspension and tablet formulations, and controlled-release capsule formulations, and an IV solution using sulfobutylether cyclodextrin (Captisol®) for solubilization of ganaxolone. The development effort led to oral suspension comprising 0.3 micron immediate release particles of ganaxolone, which is described in Example 1, and an oral capsule formulation comprising 0.3 micron immediate release particles of ganaxolone, which is described in Example 2.

Example 1

A 50 mg/ml ganaxolone suspension was prepared having the ingredients set forth in Table 1 below:

TABLE 1

Composition of 50 mg/ml Ganaxolone Suspension

| Ingredient | Grade | % w/w | mg/ml |
|---|---|---|---|
| Ganaxolone | GMP | 4.91 | 50.0 |
| Hypromellose (Pharmacoat 603) | USP/EP | 5.0 | 50.91 |
| Polyvinyl alcohol | USP/EP | 1.0 | 10.18 |
| Sodium lauryl sulfate | USP/EP | 0.1 | 1.02 |
| Methylparaben | NF/EP | 0.1 | 1.02 |
| Propylparaben | NF/EP | 0.02 | 0.20 |
| Sodium benzoate | USP/EP | 0.09 | 0.92 |
| Citric acid, anhydrous | USP/EP | 0.12 | 1.22 |
| Sodium citrate dihydrate | USP/EP | 0.0093 | 0.095 |
| Cherry artificial flavor Firmenich No. 57679 A | Pharmaceutical | 0.0025 | 0.025 |
| Sucralose | NF | 0.02 | 0.20 |
| 30% Simethicone emulsion, (Dow Corning Q7-2587) | USP | 0.0333 | 0.34 |
| Purified water | USP | q.s. 100.0 | q.s. 1.0 mL |

Table 2 shows the function of the excipients used in the 50 mg/ml ganaxolone suspension.

TABLE 2

Summary of Ingredient Function of the 50 mg/ml Ganaxolone Suspension

| Ingredient | Function |
|---|---|
| Ganaxolone | Active Pharmaceutical Ingredient |
| Hypromellose (Pharmacoat 603), USP/EP | Polymeric nanoparticle steric stabilizer |
| Sodium Lauryl Sulfate, USP, EP, NF | Anionic nanoparticle electrostatic stabilizer |
| 30% Simethicone Emulsion (Dow Corning Q7-2587) | Anti-foaming agent |
| Methylparaben USP/NF | Nanoparticle stabilizer & antimicrobial preservative |
| Sodium Benzoate | Nanoparticle stabilizer & antimicrobial preservative |
| Citric Acid Anhydrous, USP/EP | pH adjustment |
| Propylparaben NF | Nanoparticle stabilizer & antimicrobial preservative |
| Sodium Citrate Dihydrate, USP/FCC | pH adjustment |
| Polyvinyl Alcohol 4-88; Emprove ® exp PhEur, USP, JPE | stabilizer |
| Sucralose Powder, NF (micronized) | Sweetener |
| Artificial Cherry Flavor (Firmenich 502068 C) | Flavor |
| Purified Water USP/EP | diluent |

The oral bioavailability of the 50 mg/ml ganaxolone suspension is dependent upon the rate and extent of nanoparticulate drug dissolution in the relevant physiological environment. The particle sizing method and specification is intended to ensure that ganaxolone drug product exhibits an absence of agglomeration following dispersal in simulated gastrointestinal fluids.

A dispersion nanomilling process was used to reduce the particle size of ganaxolone and obtain stable ganaxolone nanoparticles. The nanomilling process included the use of yttria-stabilized zirconia (YTZ) milling media under high-energy agitation within the nanomill. In order to ensure a consistent slurry particle size prior to dispersion nanomilling, Marinus developed a high-energy rotor/stator premilling process using a VakuMix DHO-1. Following nanomilling, the dispersion was diluted from 25% w/w ganaxolone to 20% w/w ganaxolone and filtered through a 20-micron filter, and stabilizing agents (methylparaben, sodium benzoate and citric acid anhydrous) were added to promote controlled growth during a 5-10-day curing period at room temperature to approximately 300 nm. The stabilized 300 nm nanoparticles exhibit good stability against particle growth in pediatric suspension drug product and encapsulated drug product formats. The stabilization process was controlled by accurate addition and dissolution of parabens, which are water soluble stabilization agents. The curing process was controlled by regulation of hold time and temperature of the stabilized dispersion prior to suspension dilution (in the case of 50 mg/ml ganaxolone suspension) or fluid bed bead coating (in the case of the 225 mg ganaxolone capsules described in Example 2).

Three dispersion batches prepared in the dispersion nanomilling scale-up study were diluted and stabilized with the addition of sodium methylparaben, sodium benzoate and citric acid anhydrous and cured for 7 days. After curing, the particle size was measured and is shown in Table 3.

TABLE 3

Stabilized Dispersion Particle Size after 7 Days Curing

| Batch | D(10) (nm) | D(50) (nm) | D(90) (nm) |
|---|---|---|---|
| Dispersion Batch 1 | 212 | 298 | 689 |
| Dispersion Batch 2 | 208 | 289 | 539 |
| Dispersion Batch 3 | 209 | 291 | 498 |

D = diameter

As shown, the D(50) particle size was stabilized within the specification of 250-450 nm.

Example 2

Ganaxolone capsules (225 mg) were prepared having the ingredients set forth in Tables 4 and 5 below:

TABLE 4

Composition of 225 mg Ganaxolone Capsule IR Bead

| Ingredient | Grade | % w/w |
|---|---|---|
| Ganaxolone | GMP | 45.06 |
| Hypromellose (Pharmacoat 603) | USP/EP | 10.28 |
| Sodium lauryl sulfate | USP/EP/NF | 0.70 |
| Methylparaben Sodium | USP | 0.26 |
| Sodium benzoate | USP/EP | 0.20 |
| Citric acid, anhydrous | USP/EP | 0.39 |
| Sodium Chloride | USP/EP | 1.03 |
| 30% Simethicone emulsion, (Dow Corning Q7-2587) | USP | 0.11 |
| Sucrose - extra fine granulated | EP/NF | 23.04 |
| Polyethylene Glycol 3350 | NF/EP | 1.08 |

TABLE 4-continued

Composition of 225 mg Ganaxolone Capsule IR Bead

| Ingredient | Grade | % w/w |
|---|---|---|
| Polyethylene Glycol 400 | NF/EP | 0.54 |
| Polysorbate 80 | NF/EP, JP | 0.65 |
| Microcrystalline Cellulose Spheres, Grade: CP-305 | NF/EP | 16.65 |
| Total | | 100.0 |

Table 5 summarizes the function of the excipients used in the 225 mg ganaxolone capsule formulation.

TABLE 5

Summary of Ingredient Function of the 225 mg Ganaxolone Capsule

| Ingredient | Function |
|---|---|
| Ganaxolone | Active Pharmaceutical Ingredient |
| Hypromellose (Pharmacoat 603) USP/EP | Polymeric nanoparticle steric stabilizer |
| Sodium Lauryl Sulfate USP, EP, NF | Anionic nanoparticle electrostatic stabilizer |
| 30% Simethicone Emulsion USP (Dow Corning Q7-2587) | Anti-foaming agent |
| Sodium Methylparaben (Nipagin M Sodium) | Nanoparticle stabilizer & antimicrobial preservative |
| Sodium Benzoate USP/EP | Nanoparticle stabilizer & antimicrobial preservative |
| Citric Acid Anhydrous USP/EP | pH adjustment |
| Sucrose | Binder/filler |
| Sodium Chloride | Ionic strength modifier |
| Polyethylene Glycol 3350 | Plasticizer |
| Polyethylene Glycol 400 | Plasticizer |
| Polysorbate 80 | Nonionic surfactant, stabilizer |
| Microcrystalline Cellulose Spheres (Celphere CP305) | IR bead core |
| Hard Gelatin Capsule, Size 00 | Dosage form capsule |

IR = Immediate Release

The manufacturing process used for the preparation of these capsules utilizes the same drug product specifications and the same quantitative compositions, and the same nano-milling dispersion dilution and dispersion stabilization processes. Thus, the product of Example 2 utilizes a common stabilized dispersion intermediate with the product of Example 1. The methylparaben sodium may be substituted with methylparaben.

Table 6 summarizes results of thirty-six month formal stability data of ganaxolone immediate release (IR) 225 mg Capsule:

TABLE 6

Thirty-Six Month Formal Stability Data of Ganaxolone Immediate Release (IR) 225 mg Capsule (25° C./60% RH)

| Test | Specifications | Initial | 1 month | 3 month | 6 month | 9 month | 12 month | 18 Month | 24 Month | 36 Month |
|---|---|---|---|---|---|---|---|---|---|---|
| Assay (% Label Claim) | 90-110% LC | 101.4 | 100.9 | 100.3 | 99.2 | 99.8 | 99.3 | 100.6 | 100.6 | 98.4 |
| Dissolution | NLT Q = 80% at 45 minutes | 95% | 94% | 90% | 89% | 92% | 94% | 86% | 91% | 87% |
| Profile 15 min | Report Results | 74, 84, 85, 88, 87, 86 | 79, 79, 77, 82, 82, 92 | 80, 85, 81, 70, 83, 78 | 81, 79, 77, 63, 72, 73 | 78, 82, 88, 86, 82 | 90, 63, 76, 83, 70, 88 | 69, 80, 71, 70, 72, 77, 68, 89, 48, 79, 70, 73 | 66, 62, 84, 55, 64, 74 | 57, 58, 42, 74, 35, 64, 60, 60, 47, 27, 79, 60 |
| Profile 30 min | Report Results | 93, 92, 92, 94, 96, 93 | 92, 94, 86, 88, 88, 97 | 86, 89, 88, 89, 85, 88 | 91, 87, 87, 80, 81, 86 | 88, 88, 90, 92, 94, 92 | 95, 88, 85, 91, 83, 93 | 80, 86, 77, 76, 78, 85, 83, 90, 76, 88, 81, 87 | 84, 83, 92, 83, 87, 89 | 75, 78, 81, 83, 66, 85, 79, 71, 86, 60, 86, 85 |
| Profile 45 min | NLT 80% | 96, 94, 94, 95, 95, 95 | 94, 96, 92, 93, 93, 96 | 90, 90, 88, 91, 91, 90 | 93, 90, 89, 85, 85, 90 | 88, 90, 94, 93, 96, 94 | 95, 95, 95, 92, 91, 97 | 84, 88, 79, 83, 80, 86, 88, 91, 85, 90, 88, 88 | 89, 90, 92, 90, 91, 93 | 82, 88, 87, 88, 83, 90, 89, 79, 93, 84, 90, 91 |
| Profile 60 min | Report Results | 94, 92, 95, 95, 95, 96 | 95, 95, 94, 93, 95, 95 | 92, 90, 89, 90, 91, 89 | 94, 91, 90, 85, 86, 91 | 88, 92, 94, 93, 95, 93 | 95, 94, 94, 94, 91, 97 | 85, 88, 80, 85, 84, 85, 90, 91, 89, 91, 89, 88 | 93, 93, 94, 96, 93, 93 | 91, 92, 88, 89, 92, 91, 82, 91, 88, 90, 92 |

TABLE 6-continued

Thirty-Six Month Formal Stability Data of Ganaxolone Immediate Release (IR) 225 mg Capsule (25° C./60% RH)

| Test | Specifications | 25° C./60% RH | | | | | | | | |
|---|---|---|---|---|---|---|---|---|---|---|
| | | Initial | 1 month | 3 month | 6 month | 9 month | 12 month | 18 Month | 24 Month | 36 Month |
| Particle Size (D50) nm | 250-450 nm volume weighted median diameter (D50) | 339 nm | 354 nm | 336 nm | 339 nm | 335 nm | 344 nm | 368 nm | 348 nm | 360 |

Example 3

Summary of Past Epilepsy Clinical Trials in TSC-related Epilepsy

| | AFINITOR ® Phase 3 | EPIDIOLEX ® Phase 2 | EPIDIOLEX ® Phase 3 |
|---|---|---|---|
| Number patients enrolled | 366 | 18 | 224 |
| Baseline Duration | 8 weeks | 1 month | 4 weeks |
| Baseline median seizure frequency (per month) | ~41 | 94 | ~61 |
| Treatment Duration (primary) | 18 weeks | 3 months | 16 weeks |
| Median % change in seizure freq (Placebo Response) | −14.9% | N/A (open-label) | −26.5% |
| Median % change in seizure freq (Drug Response) | Low-exposure: −29.3% High-exposure: −39.6% | −48.8% | 25 mg/kg/day: −48.6% High-exposure: −47.5% |

Example 4

A Phase 2 clinical study of ganaxolone in TSC-related epilepsy is conducted. Approximately 30 male and/or female patients aged 2 through 65 years, inclusive, with TSC-related epilepsy are screened and enrolled. The patients have a confirmed clinical diagnosis of TSC and a mutation in either the TSC1 or TSC2 gene. Patients complete a daily diary of ganaxolone effect on seizures.

The treatment phase includes 2 parts: Part A and Part B. In Part A, patients receive ganaxolone for a total of 12 weeks (4-week titration, 8 weeks maintenance) in addition to their standard anti-seizure treatment. Patients are titrated to 63 mg/kg/day (max 1800 mg/day) over 4 weeks, and then maintained at that dose for another 8 weeks. Ganaxolone is administered in increments of 15 mg/kg/day up to 63 mg/kg/day given as an oral suspension with food. Patients ≤28 kg are dosed on an mg/kg basis. Patients >28 kg are dosed on a fixed regimen in increments of 450 mg/day up to 1800 mg/day. Ganaxolone is administered during the 4-week titration period as follows:

Oral Suspension Dosing$^a$ for Patients Weighing ≤28 kg (62 pounds)$^b$

| Dose | Total mg/kg/day | Days |
|---|---|---|
| 6 mg/kg TID | 18 | 1-7 |
| 11 mg/kg TID | 33 | 8-14 |
| 16 mg/kg TID | 48 | 15-21 |
| 21 mg/kg TID | 63 | 22-28 |

-continued

Oral Suspension Dosing$^a$ for Patients Weighing >28 kg (62 pounds)$^c$

| Dose | mL per Dose | Total mg/day | Days |
|---|---|---|---|
| 150 mg TID | 3 | 450 | 1-7 |
| 300 mg TID | 6 | 900 | 8-14 |
| 450 mg TID | 9 | 1350 | 15-21 |
| 600 mg TID | 12 | 1800 | 22-28 |

TID = 3 times daily.
$^a$To be administered in 3 divided doses following a meal or snack.
$^b$Patients weighing ≤28 kg will be dosed according to the patient's weight in kilograms.
$^c$Patients >28 kg will be dosed on a fixed regimen in increments of 450 mg/day up to 1800 mg/day.

Any patient not tolerating the next dose step is maintained at the lower dose step for additional days before advancing to the next dose. If the next dose is still not tolerated, the patient can drop back to the next lower dose step. A minimum dose of 33 mg/kg/day or 900 mg/day is generally required following the escalation period, during the maintenance period unless a lower dose is agreed to with the sponsor due to tolerability issues, e.g., somnolence.

Dose changes including alternative dosing paradigms (e.g., lower dose during the daytime and higher dose in the evening) are discussed with the Sponsor medical monitor prior to making the change or within 48 hours of making the change. Patients who discontinue ganaxolone treatment before the completion of the maintenance period in Part A will continue to be followed per protocol and, at a minimum, patients will be encouraged to maintain daily seizure diary entries until Part A is completed. These patients will also return to the site 2 weeks after the taper for safety follow-up assessments.

Patients with a seizure frequency reduction rate of ≥35% during the 12-week treatment period in Part A compared to baseline (e.g., 4-week baseline period) and who do not have any other contraindications for continued treatment continue to be treated with ganaxolone in the OLE phase (Part B) of the study may continue into Part B ("OLE eligible"). Part B is an open-label extension and lasts about 24 weeks. Thus, Part B is available to patients that respond to ganaxolone as defined by a protocol. The main difference between Part A and Part B is the length of treatment, less frequent assessments, and the ability to alter drug doses (both ganaxolone and other AED treatments which includes initiating and stopping other medications) based on evaluation of the patient's clinical course during Part B.

In part B, ganaxolone patients continue ganaxolone treatment at the dose that they were on at completion of Part A. During Part B, doses of ganaxolone may be adjusted to a maximum of 600 mg TID for patients weighing >28 kgs and a maximum dose of 21/mg/kg TID for patients ≤28 kg. Doses of other anti-seizure medications may be adjusted (including tapering and initiating treatments) during Part B based on Investigator discretion.

Any patient who completes Part A and does not continue in Part B or completes Part B or discontinues GNX treatment undergo a 2 week drug de-escalation (taper) period, unless medically contraindicated, and return to the site 2 weeks later for safety follow-up assessments.

Patients completing Part A and deemed eligible for Part B continue taking ganaxolone at the same dose they were on at the completion of Part A for an additional 24 weeks of treatment in Part B.

Patients may receive lower dose during the daytime and higher dose in the evening.

Anyone discontinuing ganaxolone undergoes a 2-week taper, unless otherwise medically contraindicated such as drug-induced rash.

Patients who discontinue ganaxolone before the completion of the treatment maintenance period are continued to be followed per protocol and, at a minimum, patients are encouraged to maintain daily seizure diaries until the treatment period in Part A is completed. These patients return to the site 2 weeks after the taper for safety follow-up assessments.

Patients may return for a 2 week follow-up safety visit (e.g., due to early discontinuation in Parts A or B, does not participate in Part B or completes Part B).

The primary efficacy endpoints are to assess potential for ganaxolone in TSC-related epilepsy over a 12-week period and/or % change in primary seizure frequency through the end of the 12-week treatment (titration and maintenance) period in Part A. Primary seizure types include focal motor seizures without impairment of consciousness or awareness, focal seizures with impairment of consciousness or awareness, focal seizures evolving to bilateral generalized convulsive seizures, and generalized seizures with a motor component that are countable.

The secondary objectives are to assess the safety and tolerability of ganaxolone as adjunctive therapy at through the end of the 12-week treatment (titration and maintenance) period in Part A; To assess pharmacokinetic (PK) parameters in patients receiving ganaxolone doses up to 63 mg/kg/day (or 1800 mg/day maximum) throughout the study; to assess pharmacokinetic (PK) parameters in patients receiving ganaxolone doses up to 63 mg/kg/day (or 1800 mg/day maximum) throughout the study; to assess the long-term safety and tolerability of GNX when administered as adjunctive therapy throughout Part B.

The exploratory objectives are to assess changes to quality of life; to assess behavioral/neuropsychiatric changes in patients receiving ganaxolone as adjunctive therapy at the end of the 12-week treatment (titration and maintenance) period in Part A; to assess the relationship between efficacy response to ganaxolone and biomarker levels (e.g. neurosteroids); to assess the potential for ganaxolone effects on EEG activity; to assess changes in other types of seizures (non-primary) in TSC; to assess the effect of ganaxolone on primary seizure-free days; to assess the effect of ganaxolone on infantile/epileptic spasm free days; to assess the effect of ganaxolone on infantile/epileptic spasm free days.

A. Pharmacokinetic Assessments:

The PK population will include all patients who have received at least 1 dose of GNX and who have had at least 1 sample collected and a valid bioanalytical result obtained. The samples will be drawn between 1 and 5 hours or between 4 and 8 hours after the last dose during Part A and Part B. Pharmacokinetic analyses will be limited to listing of concentrations because sufficient concentration-time data will not be available for noncompartmental analyses such as Cmax, AUC or tmax. Pharmacokinetic data from this study may be used for a Population PK analyses to be conducted separately from this study and reported separately.

B. Neurosteroid Serum and Concomitant AED Levels:

Blood samples will be drawn at screening visit, Week 12 in Part A, and the final visit in Part B to measure neurosteroid levels (including allopregnanolon and related endogenous CNS-active steroids and sulfate metabolites, including, e.g., alloprenanolone-sulfate).

Example 5. Biomarker

Individuals (n=11) with a confirmed PCDH19 mutation and minimum seizure burden were enrolled between May 2015 and November 2015 at six centers in the U.S. and Italy. Seizure frequency change (%) was assessed as the primary endpoint and a responder was defined as having a 25% or greater decrease in seizure rate. Plasma neurosteroid levels were quantified using a previously published GC/MS method (doi:10.1016/50028-3908(99)00149-5). In two cases, baseline neurosteroid levels were not measured. In these cases, the values from 6 months were used as neurosteroid levels were observed not to change significantly over time.

The median change in 28-day seizure frequency (all seizure types) from baseline for all-corners (n=11) was a decrease of 26%. In this group, average plasma allopregnanolone-sulfate (Allo-S) concentration was 4,741 pg mL-1 (median=433 pg mL-1). The responder analysis and correlation with Allo-S demonstrated two discrete populations. Responders (n=6) (≥25% decrease in seizure rate) and non-responders (n=5) had plasma Allo-S concentrations of 501±430 pg mL-1 and 9,829±6,638 pg mL-1, respectively (mean±SD, p=0.05, Mann-Whitney).

The biomarker-positive group significantly improved (p=0.02, Wilcoxon) whereas the biomarker-negative (high Allo-S) group did not improve, but also did not significantly deteriorate (p=0.25, Wilcoxon), when comparing seizure frequency at 6 months to baseline. Retrospective analysis of biomarker-positive (n=7, Allo-S<2,500 pg mL-1) versus biomarker-negative (n=4, Allo-S >2,500 pg mL-1) subjects yielded median % change seizure rates of −53.9% and 247%, respectively (p=0.006, Mann-Whitney). Further, the biomarker-positive group significantly improved (p=0.02, Wilcoxon Signed Rank) whereas the biomarker-negative group did not significantly deteriorate (p=0.25, Wilcoxon Signed Rank) when comparing seizure frequency at 6 months to baseline.

Example 6. Case Report 1 for TSC Subject Enrolled in Part A of the Open-Label Phase 2 Trial A subject (subject 001) with tuberous-sclerosis complex was enrolled in Part A of the open-label Phase 2 trial of adjunctive ganaxolone (GNX) treatment in tuberous sclerosis complex-related epilepsy in accordance with the study protocol described in Example 4. The subject had a baseline seizure burden of 132.41 per 28 days. Ganaxolone was administered orally three times a day at a maximum daily dose of 1800 mg for 11 weeks (78 days). The subject has completed the protocol and experienced a 64% reduction in seizure relative to baseline. This is the first subject to have completed the protocol. Additional subject are currently enrolled but have not completed the study.

TABLE 8

Summary of changes in seizure in TSC subject

| Subject | Baseline seizure frequency (per 28 days) | Treatment duration (days) | % Change from baseline |
|---|---|---|---|
| 001 | 132.41 | 78 | −64% |

Example 7. Preliminary Pharmacokinetic and Pharmacodynamic (PK/PD) Analysis

A preliminary PK/PD analysis was conducted to explore the relationship, if any, between ganaxolone levels and percent change in major motor seizure frequency.

a) Study Design

Global, randomized, double-blind, placebo-controlled phase 3 clinical trial to assess the safety and efficacy of adjunctive ganaxolone for the treatment of seizures associated with CDD. Patients aged 2 to 21 years with a pathogenic or likely pathogenic mutation of the CDKL5 gene, neurodevelopmental impairment, and seizures refractory to treatment with at least 2 prior antiseizure medications who experienced at least 16 seizures per 28 days during the 2 months prior to screening were eligible to enroll. Study consisted of a 6-week baseline followed by a 17-week double-blind phase (ganaxolone or placebo, 1:1). The dose of ganaxolone 50 mg/mL suspension was titrated over 4 weeks to 63 mg/kg/day (21 mg/kg TID), not to exceed 1800 mg/d (600 mg TID), or to the maximum tolerated dose. Blood draws for PK analysis were scheduled to occur at visit 3 (week 5), visit 4 (week 9), and visit 5 (week 17).

b) Methods

Mean ganaxolone concentration was calculated for each subject using available results from up to three laboratory determinations during the double-blind phase. Linear regression was conducted using arithmetic- and natural logarithm-transformed percent reduction in major motor seizures ($\log_e$ [percent reduction+100]) as dependent variable and natural logarithm-transformed mean ganaxolone concentration as the single explanatory variable. Regression diagnostics included examination of residual and normal probability plots and determination of outliers and influential values. Cases with standardized residuals >2 or <−2 were excluded from the model and the regression was repeated.

The resulting sample was utilized in determination of a Pearson correlation coefficient (using log-transformed values). Additionally, percent seizure reduction was compared in three tertiles representing low (N=13), medium (N=13) and high (N=12) mean per subject ganaxolone concentrations using a Kruskal-Wallis test.

The number of CNS-related adverse events suggestive of potential dose-related toxicity (somnolence, sedation, lethargy, disturbance in attention, drooling and hypotonia) in ganaxolone-treated participants as well as the onset and duration of the events was tabulated, and the number of participants with CNS adverse events during each week of the double-blind phase calculated.

c) Results

Forty-four participants with seizure reduction data had at least one plasma ganaxolone level determination (mean+ standard deviation=103.5+79.2 ng/mL). In a linear regression with percent seizure reduction as the dependent variable and mean plasma ganaxolone concentration as the independent variable, six cases were determined to be outliers due to adjusted residuals >2 or <−2. Repeat linear regression excluding those cases (N=38) yielded an adjusted R2 of 0.227 (F(1,36)=11.89), p=0.001). The correlation coefficient for mean plasma ganaxolone concentration and percent reduction in major motor seizures using the same sample was −0.499 (p=0.001). A robust regression was performed including all observations (N=44) which replicated the findings of this analysis.

Figure 2:
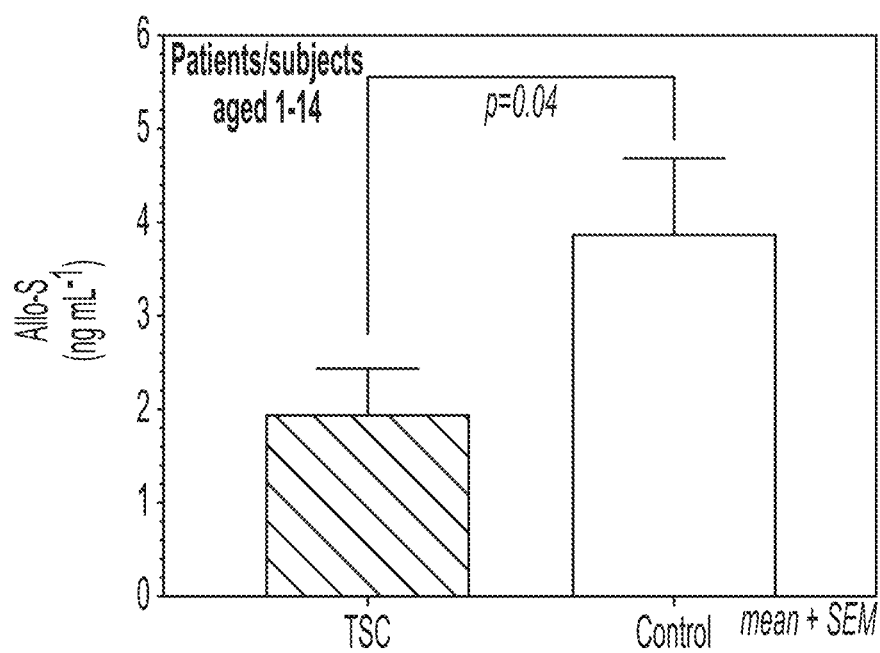
Figure 3:
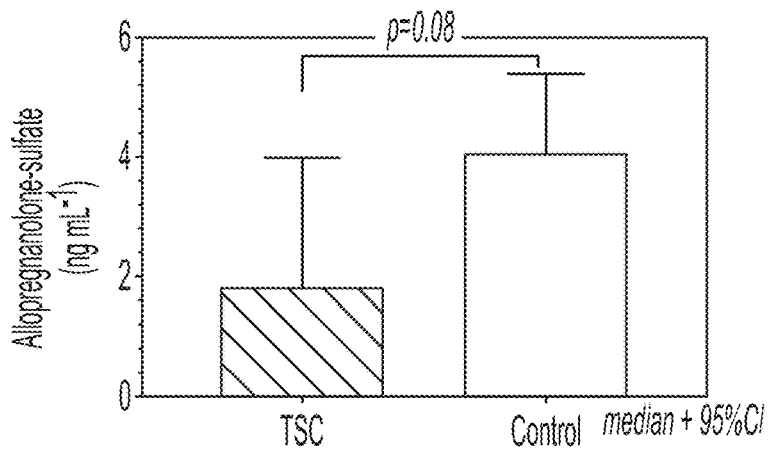
FIG. 3 depicts Allo-S Distribution in TSC Patients and Unaffected Subjects (all individuals).
Figure 4:
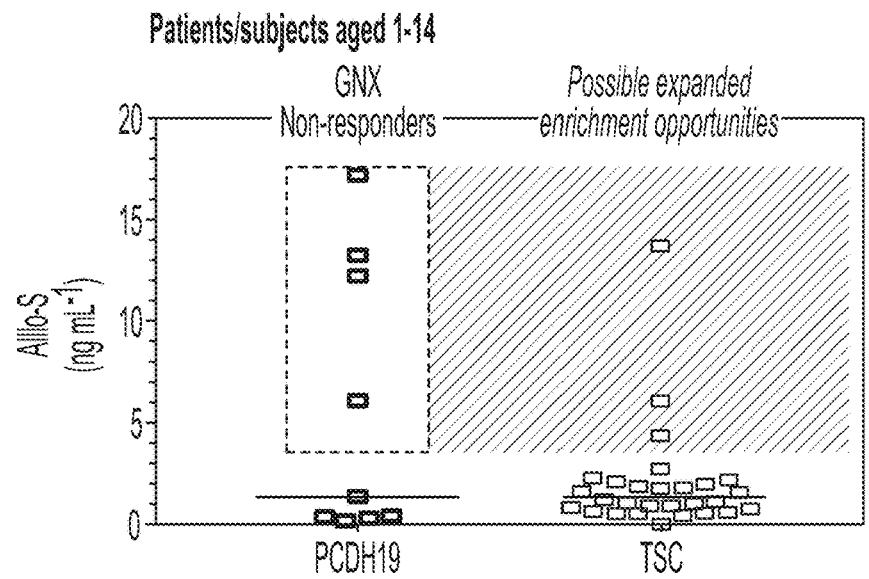
FIG. 4 depicts allopregnanolone-sulfate (Allo-S) comparison in PCDH19 and TSC and potential expansion opportunity to explore Allo-S biomarker in TSC.
Figure 5:
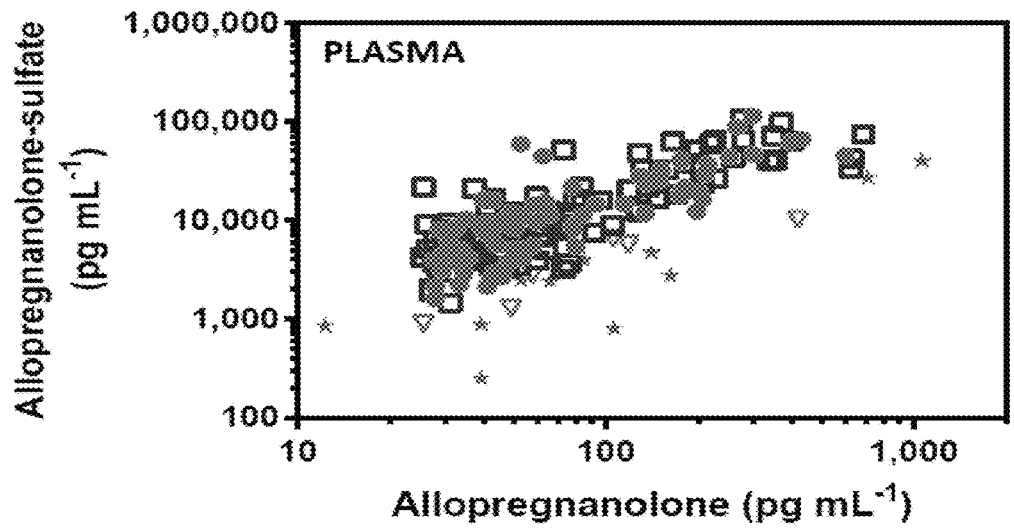
FIG. 5 depicts a positive correlation between allopregnanolone (Allo) and allopregnanolone-sulfate (Allo-S).

Mean and median percent reduction in major motor seizures was calculated for low-, medium- and high-ganaxolone concentration tertiles (Table 9). There was a statistically significant between-group difference in the percent reduction of major motor seizure frequency (H(2)=9.087, p=0.011)(FIG. 2). Post-hoc pairwise comparisons of sample distributions for the three groups showed a statistically significant difference between Low and High GNX level groups but not for other between-group tests.

TABLE 9

Tertiles Based on Mean Ganaxolone Plasma Concentration

| GNX level groups | Mean GNX level (ng/ml) | Mean percentage change in major motor seizures (per 28 days) | Median percentage change in major motor seizures (per 28 days) |
|---|---|---|---|
| Low (n = 13) | 40.2 | −6.5 | −8.4 |
| Median (n = 13) | 72.3 | −30.3 | −39.5 |
| High (n = 12) | 172.6 | −44.3 | −46.0 |

In summary, logarithms of plasma ganaxolone levels and percent change in major motor seizure frequency were negatively correlated. Increases in plasma GNX levels were associated with greater reductions in seizure frequency in the range of 27 to 333 ng/mL in patients with CDKL5 deficiency disorder (CDD). The back-transformation of log values indicates that a plasma concentration of approximately 100 ng/mL (mean of CDD population) predicts an approximately 40% seizure reduction in the participants in this study.

Modeled PK curves based on previous Phase 1 studies demonstrate that TID dosing is able to increase trough GNX levels compared to BID dosing. Results from the preliminary PK/PD analysis suggest that increasing plasma ganaxolone concentrations were associated with improved seizure reduction and that concentrations of approximately 100 ng/mL are associated with meaningful changes in seizure frequency. Based on the modeled PK curves, TID dosing may yield plasma ganaxolone levels >100 ng/mL for approximately 78% of a 24-hr day compared to just 53% using BID dosing. While these analyses do not preserve randomization, and hence might not represent causal effects of GNX on changes in seizure frequency, they are suggestive that TID dosing might provide increased antiseizure benefits.

The invention claimed is:

1. A method for treating tuberous sclerosis-related epilepsy comprising administering to a subject in need thereof a therapeutically effective amount of ganaxolone.

2. The method of claim 1, wherein the therapeutic effectively amount is administered orally three times per day.

3. The method of claim 1, wherein ganaxolone is administered as an oral suspension.

4. The method of claim 1, wherein ganaxolone is administered as an oral capsule.

5. The method of claim 1, wherein ganaxolone is administered as a tablet.

6. The method of claim 1, wherein the therapeutically effective amount is an amount sufficient to produce a ganaxolone plasma concentration of at least about 100 ng/ml for at least about 70% or more per day.

7. The method of claim 1, wherein the therapeutically effective amount is no more than about 1800 mg per day.

8. The method of claim 7, wherein the therapeutically effective amount is about 600 mg three times per day.

9. The method of claim 1, wherein the therapeutically effective amount is no more than about 1500 mg per day.

10. The method of claim 9, wherein the therapeutically effective amount is about 500 mg three times per day.

11. The method of claim 1, wherein the therapeutically effective amount is no more than about 63 mg/kg per day.

12. The method of claim 11, wherein the therapeutically effective amount is about 21 mg/kg three times per day.

13. A method for treating tuberous sclerosis-related epilepsy comprising administering to a subject in need thereof a therapeutically effective amount of ganaxolone that is sufficient to produce a ganaxolone plasma concentration of at least about 100 ng/ml over a period of at least about 70% of a day.

14. The method of claim 13, wherein the subject is administered ganaxolone three times per day.

15. The method of claim 13, wherein ganaxolone is administered orally.

16. The method of claim 15, wherein ganaxolone is administered as an oral suspension.

17. The method of claim 15, wherein ganaxolone is administered as an oral capsule.

18. The method of claim 17, wherein ganaxolone is administered as a tablet.

19. The method of claim 13, wherein ganaxolone is administered as an intravenous infusion.

20. The method of claim 13, wherein the therapeutically effective amount is no more than about 1800 mg per day.

21. The method of claim 20, wherein the therapeutically effective amount is about 600 mg three times per day.

22. The method of claim 13, wherein the therapeutically effective amount is no more than about 1500 mg per day.

23. The method of claim 22, wherein the therapeutically effective amount is about 500 mg three times per day.

24. The method of claim 13, wherein the therapeutically effective amount is about 63 mg/kg per day.

25. The method of claim 24, wherein the therapeutically effective amount is about 21 mg/kg three times per day.

* * * * *